US012496200B2

(12) United States Patent
Babaee et al.

(10) Patent No.: US 12,496,200 B2
(45) Date of Patent: Dec. 16, 2025

(54) KIRIGAMI-INSPIRED STENTS FOR SUSTAINED LOCAL DELIVERY OF THERAPEUTICS

(71) Applicants: Massachusetts Institute of Technology, Cambridge, MA (US); Brigham and Women's Hospital, Boston, MA (US)

(72) Inventors: Sahab Babaee, Arlington, MA (US); Yichao Shi, Burlington (CA); Saeed Abbasalizadeh, Tehran (IR); Robert Langer, Newton, MA (US); Carlo Traverso, Newton, MA (US)

(73) Assignees: Massachusetts Institute of Technology, Cambridge, MA (US); Brigham and Women's Hospital, Boston, MA (US)

( * ) Notice: Subject to any disclaimer, the term of this patent is extended or adjusted under 35 U.S.C. 154(b) by 356 days.

(21) Appl. No.: 17/353,500

(22) Filed: Jun. 21, 2021

(65) Prior Publication Data

US 2021/0393422 A1 Dec. 23, 2021

Related U.S. Application Data

(60) Provisional application No. 63/041,154, filed on Jun. 19, 2020.

(51) Int. Cl.

| | |
|---|---|
| ***A61F 2/848*** | (2013.01) |
| ***A61F 2/91*** | (2013.01) |
| *A61F 2/04* | (2013.01) |

(52) U.S. Cl.
CPC ................ *A61F 2/848* (2013.01); *A61F 2/91* (2013.01); *A61F 2002/046* (2013.01);
(Continued)

(58) Field of Classification Search
CPC ...... A61F 2/848; A61F 2/91; A61F 2002/046; A61F 2002/8483; A61F 2220/0016;
(Continued)

(56) References Cited

U.S. PATENT DOCUMENTS

| | | | |
|---|---|---|---|
| 8,579,956 | B2 | 11/2013 | Hossainy |
| 2008/0077164 | A1 | 3/2008 | Murphy |

(Continued)

FOREIGN PATENT DOCUMENTS

| | | |
|---|---|---|
| WO | 2021258063 A1 | 12/2021 |

OTHER PUBLICATIONS

Babaee, S., Pajovic, S., Rafsanjani, A., Shi, Y., Bertoldi, K., & Traverso, G. Bioinspired kirigami metasurfaces as assistive shoe grips. Nat. Biomed. Eng. (2020).

(Continued)

*Primary Examiner* — Thomas Mcevoy
(74) *Attorney, Agent, or Firm* — Quarles & Brady, LLP

(57) ABSTRACT

The present disclosure provides a kirigami-inspired injectable stent system. The stent systems and methods enable radial/circumferential and longitudinal delivery of an extended release of therapeutics within tubular structures of the body, such as the GI tract and trachea. According to some aspects, a kirigami-based injectable stent system is provided that can enable drug release through deposition of therapeutic-coated needles of the stent in the tubular mucosa, such as often found in the gastrointestinal tract or trachea.

12 Claims, 31 Drawing Sheets

(52) U.S. Cl.
CPC ................. *A61F 2002/8483* (2013.01); *A61F 2220/0016* (2013.01); *A61F 2230/0023* (2013.01); *A61F 2230/0091* (2013.01)

(58) Field of Classification Search
CPC ...... A61F 2230/0023; A61F 2230/0091; A61F 2002/8486; A61M 37/0015; A61M 2037/0023; A61M 2037/003; A61M 2037/0038; A61M 2037/0046; A61M 2037/0061
See application file for complete search history.

(56) References Cited

U.S. PATENT DOCUMENTS

| | | | | |
|---|---|---|---|---|
| 2010/0131045 | A1* | 5/2010 | Globerman | A61F 2/915 72/367.1 |
| 2011/0034860 | A1* | 2/2011 | Melsheimer | A61K 9/0021 604/22 |
| 2011/0238157 | A1* | 9/2011 | Li | A61F 2/915 623/1.16 |
| 2014/0081416 | A1 | 3/2014 | Clerc et al. | |
| 2014/0172066 | A1* | 6/2014 | Goepfrich | A61F 2/958 623/1.11 |
| 2015/0100133 | A1* | 4/2015 | Xie | A61B 17/24 623/23.7 |
| 2016/0120638 | A1 | 5/2016 | Michalak | |
| 2016/0317330 | A1 | 11/2016 | Clerc et al. | |
| 2017/0100266 | A1 | 4/2017 | Fulkerson et al. | |
| 2017/0128635 | A1 | 5/2017 | Savage et al. | |
| 2018/0211813 | A1* | 7/2018 | Kirkpatrick | A61F 2/82 |
| 2019/0232598 | A1 | 8/2019 | Abbasi et al. | |
| 2019/0314181 | A1 | 10/2019 | Ganz et al. | |
| 2020/0107947 | A1 | 4/2020 | Jimenez, Jr. et al. | |
| 2020/0155815 | A1 | 5/2020 | Giasolli et al. | |
| 2021/0346180 | A1* | 11/2021 | Al-Hakim | A61F 2/915 |

OTHER PUBLICATIONS

Celli P., C. McMahan, B. Ramirez, A. Bauhofer, C. Naify, D. Hofmann, B. Audoly, C. Daraio. Shape-morphing architected sheets with non-periodic cut patterns. Soft Matter 14, 9744 (2018).

Connolly F, Polygerinos P, Walsh CJ, Bertoldi K. Mechanical programming of soft actuators by varying fiber angle. Soft Robot 2(1):26-32 (2015).

Fu, H., Nan, K., Bai, W. et al. Morphable 3D mesostructures and microelectronic devices by multistable buckling mechanics. Nat. Mater. 17, 268-276 (2018).

Gómez-Gaete C., M. Retamal, C. Chávez, P. Bustos, R. Godoy, P. Torres-Vergara. Development, characterization and in vitro evaluation of biodegradable rhein-loaded microparticles for treatment of osteoarthritis. European J. of Pharm. Sci. 96, 390-397 (2016).

International Search Report and Written Opinion for corresponding PCT/US2021/038286, issued Oct. 5, 2021, 13 pages.

Leary S., W. Underwood, R. Anthony, S. Cartner, D. Corey, T. Grandin, C. Greenacre, S. Gwaltney-Brant, M. A. McCrackin, R. Meyer, D. Miller, J. Shearer, R. Yanong, AVMA Guidelines for the Euthanasia of Animals: 2013 Edition (American Veterinary Medical Association, Schaumburg, Illinois, 2013).

Liu, Z. et al. Nano-kirigami with giant optical chirality. Sci. Adv. 4, 1-8 (2018).

McMurry-Heath, M., and Hamburg M. Creating a Space for Innovative Device Development. Sci. Transl. Med. 4 (2012).

Mintz Y., S. Horgan, J. Cullen, E. Falor, M. A. Talamini, Dual-lumen natural orifice translumenal endoscopic surgery (NOTES): a new method for performing a safe anastomosis. Surg. Endosc. 22, 348-351 (2008).

Morikawa et al, Donut-Shaped Stretchable Kirigami: Enabling Electronics to Integrate with the Deformable Muscle, Adv. Health. Mate. (2019).

Rafsanjani, A. & Bertoldi, K. Buckling-Induced Kirigami. Phys. Rev. Lett. 118, 1-11 (2017).

Rafsanjani, A., Zhang, Y., Liu, B., Rubinstein, S. M. & Bertoldi, K. Kirigami skins make a simple soft actuator crawl. Sci. Robot. 3, eaar7555 (2018).

Shyu, T. C. et al. A kirigami approach to engineering elasticity in nanocomposites through patterned defects. Nat. Mater. 14, 785-789 (2015).

Tang, Y., Li, Y., Hong, Y., Yang, S., Yin, J. Programmable active kirigami metasheets with more freedom of actuation. Proceedings of the National Academy of Sciences, 2019; 201906435.

Tarnoff M., S. Shikora, A. Lembo, Acute technical feasibility of an endoscopic duodenal-jejunal bypass sleeve in a porcine model: a potentially novel treatment for obesity and type 2 diabetes. Surg. Endosc. 22, 772-776 (2008).

Wu, C., Wang, X., Lin, L., Guo, H. & Wang, Z. L. Paper-Based Triboelectric Nanogenerators Made of Stretchable Interlocking Kirigami Patterns. ACS Nano 10, 4652-4659 (2016).

Zhang Y., Z. Yan, K. Nan, D. Xiao, Y. Liu, H. Luan, H. Fu, X. Wang, Q. Yang, J. Wang, W. Ren, H. Si, F. Liu, L. Yang, H. Li, J. Wang, X. Guo, H. Luo, L. Wang, Y. Huang, J. A. Rogers. A mechanically driven form of Kirigami as a route to 3D mesostructures in micro/nanomembranes. Proc. Natl. Acad. Sci. USA 112, 11757 (2015).

Zheng, W. et al. Kirigami-Inspired Highly Stretchable Nanoscale Devices Using Multidimensional Deformation of Monolayer MoS 2. Chem. Mater. 30, 6063-6070 (2018).

* cited by examiner

KIRIGAMI-INSPIRED STENTS FOR SUSTAINED LOCAL DELIVERY OF THERAPEUTICS

CROSS-REFERENCES TO RELATED APPLICATIONS

The present application is based on, claims priority to, and incorporates herein by reference in its entirety, U.S. Provisional Patent Application No. 63/041,154 filed Jun. 19, 2020, entitled "Kirigami-inspired Stents for Sustained Local Delivery of Therapeutics."

STATEMENT REGARDING FEDERALLY SPONSORED RESEARCH

This invention was made with Government support under Grant No. R01 EB000244 awarded by the National Institutes of Health. The Government has certain rights in the invention.

BACKGROUND

Implantable drug depots have been applied for decades across a range of sites in the body, including the brain. For tubular structures in the body, coated stents have been applied to provide local high concentrations of a therapeutic, as found in drug eluting stents. In the gastrointestinal ("GI") tract, coated stents have been explored, though suffer from a significant rate of complications including stent migration and tissue perforation. Moreover, the delivery of therapeutics from drug eluting stents is governed by diffusion limitations through tissue, potentially limiting delivery to therapeutics of lower molecular weight and particular physicochemical characteristics which support partitioning of the drug into the mucosa.

In the GI tract, endoscopic injection, initially pioneered through the development of the Carr-Locke Needle, transformed the capacity to locally deliver therapeutics for a range of applications including hemostasis with epinephrine, sclerosant injection for variceal ablation, submucosal lifts with normal saline and other materials, as well as steroid injections for inflammation control, and injection of biologics for inflammatory stricture management. All of these applications apply a hypodermic needle, which can be deployed endoscopically supporting single site injection.

SUMMARY

Recognizing that many GI pathologies, including inflammatory bowel disease, eosinophilic GI disorders, and Celiac disease, affect extended multi-centimeter segments of the GI tract, the present disclosure provides a solution for rapid circumferential submucosal deposition of controlled drug releasing systems.

Implantable drug depots have the capacity to locally meet therapeutic requirements by maximizing local drug efficacy and minimize potential systemic side effects. The GI tract represents a site with a broad range of pathology affecting its tubular structure. Its length and tubular structure though make the application and deposition of drug depots challenging as current injectable systems, as briefly described above, generally only facilitate single point administration.

According to aspects of the present disclosure, a kirigami-mediated injectable stent system is provided. The systems and methods described herein enable radial/circumferential and longitudinal intramucosal delivery for an extended release of therapeutics within tubular structures of the body. According to some aspects, a kirigami-based injectable stent system is provided that can enable ultra-long local drug release through deposition of drug-loaded polymeric particles in the tubular mucosa of the GI tract.

According to some aspects of the present disclosure, a stent for treating tissue within a gastrointestinal tract or trachea of a subject is provided. The stent includes a tubular body extending along a central axis and configured to move between a retracted position and an elongated position, and a plurality of projections formed into the tubular body, each projection configured to form a cutting edge to pierce a submucosal tissue within the gastrointestinal tract or trachea. Each projection among the plurality of projections is configured to undergo a change in orientation relative to the central axis when the tubular body moves between the retracted position and the elongated position.

According to some aspects of the present disclosure, a stent system for treating a tissue within a gastrointestinal tract or trachea of a subject is provided. The system includes a tubular body extending along a central axis to form a lumen within the tubular body an actuator received within the lumen and configured to move the tubular body between a retracted position and an elongated position, and a pattern of a plurality of cuts formed along the tubular body and extending through the tubular body to the lumen. The pattern of the plurality of cuts deploys into a plurality of interconnected projections that are configured to extend radially away from the tubular body relative to the central axis to engage a submucosal tissue within the gastrointestinal tract or trachea of a subject when the tubular body is moved towards the elongated position.

According to some aspects of the present disclosure, a method of inserting a stent into a gastrointestinal tract or trachea a subject is provided. The method includes positioning a stent to a target tissue site within a gastrointestinal tract or trachea, the stent having a tubular body extending along a central axis to form a lumen within the tubular body, and pressurizing an actuator received within the lumen to move the tubular body from a retracted position to an elongated position. A surface of the tubular body includes a pattern of a plurality of cuts configured to deploy into a plurality of interconnected projections as the tubular body is moved into the elongated position to engage the target tissue site of the subject.

The foregoing and other aspects and advantages of the disclosure will appear from the following description. In the description, reference is made to the accompanying drawings which form a part hereof, and in which there is shown by way of illustration a preferred configuration of the disclosure. Such configuration does not necessarily represent the full scope of the disclosure, however, and reference is made therefore to the claims and herein for interpreting the scope of the disclosure.

BRIEF DESCRIPTION OF THE DRAWINGS

The invention will be better understood and features, aspects and advantages other than those set forth above will become apparent when consideration is given to the following detailed description thereof. Such detailed description makes reference to the following drawings.

DETAILED DESCRIPTION

Figure 1:
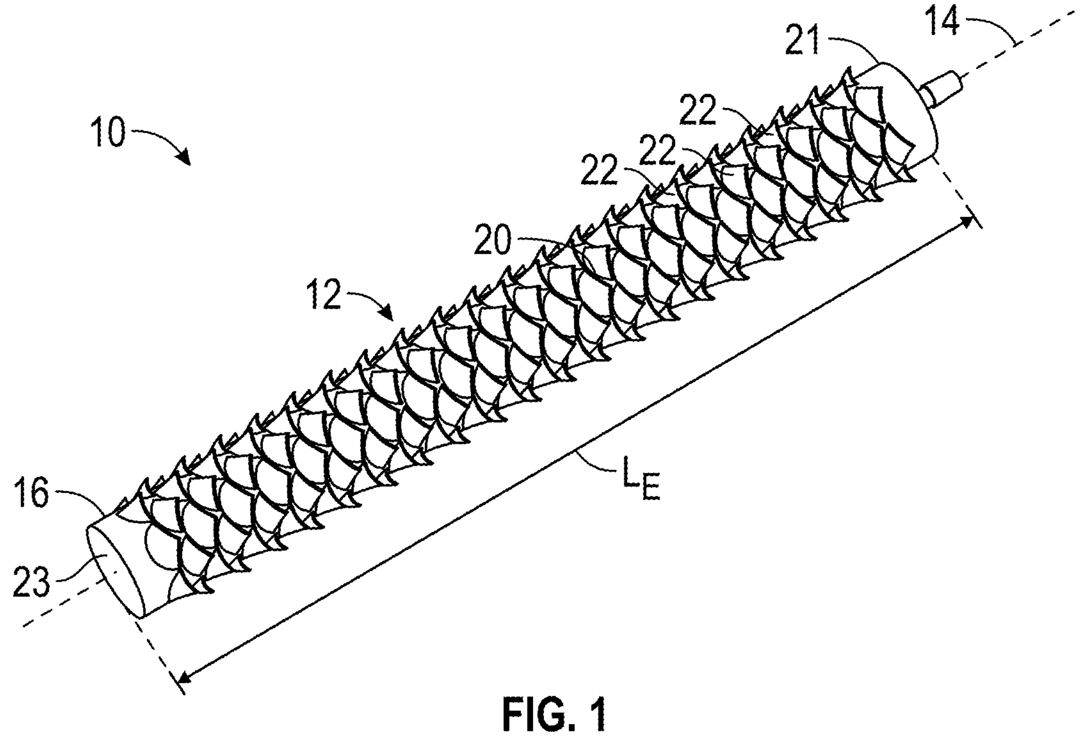
FIG. 1 illustrates a perspective view of a kirigami-inspired stent in an extended position according to one aspect of the present disclosure.

Before any aspects of the invention are explained in detail, it is to be understood that the invention is not limited in its application to the details of construction and the arrangement of components set forth in the following description or illustrated in the following drawings. The invention is capable of other aspects and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The use herein of the term "axial" and variations thereof refers to a direction that extends generally along an axis of symmetry, a central axis, an axis of rotation, or an elongate direction of a particular component or system. For example, axially extending features of a component may be features that extend generally along a direction that is parallel to an axis of symmetry or an elongate direction of that component. Further, for example, axially aligned components may be configured so that their axes of rotation are aligned. Similarly, the use herein of the term "radial" and variations thereof refers to directions that are generally perpendicular to a corresponding axial direction. For example, a radially extending structure of a component may generally extend at least partly along a direction that is perpendicular to a longitudinal or central axis of that component. The use herein of the term "circumferential" and variations thereof refers to a direction that extends generally around a circumference of an object or around an axis of symmetry, an axis of rotation, a central axis, or an elongate direction of a particular component or system.

As also used herein, unless specified or limited otherwise, the terms "approximately" and "substantially" and variations thereof, when used relative to a numerical value, define a range of values within 20% of the numerical value (e.g., within 15%, 10%, or within 5%).

In some implementations, devices or systems disclosed herein can be utilized, manufactured, or treated using methods embodying aspects of the invention. Correspondingly, any description herein of particular features, capabilities, or intended purposes of a device or system is generally intended to include disclosure of a method of using such devices for the intended purposes, of a method of otherwise implementing such capabilities, of a method of manufacturing relevant components of such a device or system (or the device or system as a whole), and of a method of installing or utilizing disclosed (or otherwise known) components to support such purposes or capabilities. Similarly, unless otherwise indicated or limited, discussion herein of any method of manufacturing or using for a particular device or system, including installing the device or system, is intended to inherently include disclosure, as embodiments of the invention, of the utilized features and implemented capabilities of such device or system.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

Kirigami is a Japanese form of paper art similar to origami that includes cutting of the paper and can enable the design of a range of functional tools and programmable systems from macroscale soft actuators and robots to microelectronics and nanostructures. Buckling-induced kirigami structures are engineered to utilize local elastic instabilities for versatile shape transformation from flat, generally smooth surfaces to complex three-dimensional architectures. According to some applications, the buckling kirigami metasurfaces have been applied to footwear outsoles to generate higher friction forces and mitigate the risk of slips and falls in a range of environments.

As explained herein, inspired from the skin of scaly-skin animals like snakes and sharks, an injectable stent was developed which is composed of a periodic array of denticle-like needles (e.g., a kirigami cylindrical shell) integrated with a linear actuator (e.g., a pneumatic soft actuator). As detailed herein, a combination of finite element ("FE") simulations and experiments, kirigami shells and linear actuators were identified to develop injectable stents in multiple length scales that can be easily deployed in the tubular lumen of the GI tract such as esophagus as well as arteries and airways. By pressurizing the soft actuator, the kirigami needles buckle out (e.g., extend) such that the resulting needles provide required stiffness and radial expansion (in some examples, up to 60% of the stent diameter) to enable injections of drug-loaded particles into the tissue of a subject (e.g., into submucosal tissues of the GI tract). These kirigami-based injectable stents serve as a class of drug-eluting stents, capable of releasing drug depots through multi-point deposition of drug particles, thereby enhancing sustained local delivery of therapeutics.

Kirigami-Inspired Stent Examples

Figure 2:
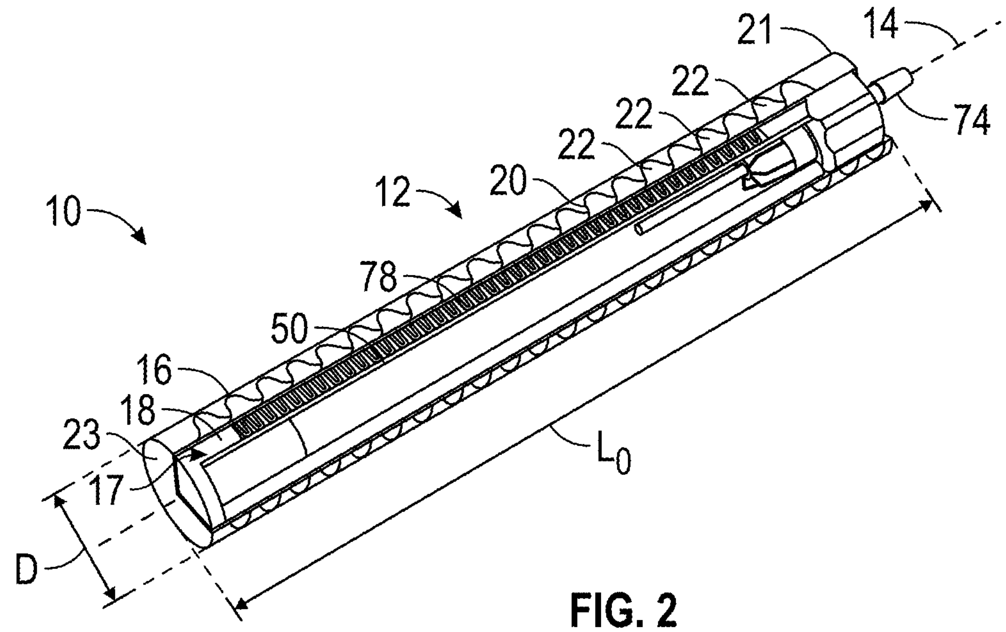
FIG. 2 illustrates a perspective view, including a cutaway, of the kirigami-inspired stent of FIG. 1 in a retracted position.

Referring to FIGS. 1 and 2, one non-limiting example of a stent 10 is illustrated. The stent 10 can define a tubular body 12 extending axially along a central axis 14 and configured for insertion into the GI tract or trachea. The tubular body 12 of the stent 10 is configured to undergo a shape change in at least one dimension. In the illustrated non-limiting example, the tubular body 12 is axially extendable between a first, retracted position (FIG. 2) and a second, extended position (FIG. 1). In the extended position, the tubular body 12 is elongated in the axial direction relative to the retracted position. As will be described, the elongation of the tubular body 12 between the retracted position and the extended position is configured to deploy projections configured to pierce or engage tissue of a subject.

The tubular body 12 can include a cylindrical outer shell 16 forming a lumen 17 (e.g., a hollow core) and an actuator 18 arranged within the lumen 17 of the outer shell 16. The outer shell 16 can include at least one cut 20. In the illustrated non-limiting example, the outer shell 16 can include a patterned array of a plurality of interconnected cuts 20 (e.g., openings). In the illustrated non-limiting example, the plurality of cuts 20 extend along at least a portion of the axial length of the tubular body 12. For example, the plurality of cuts 20 can extend along at least 50% of an entire length $L_0$ of the tubular body 12. According to some non-limiting examples, the plurality of cuts 20 can extend along between about 50% and about 100% of the entire length $L_0$ of the tubular body 12. According to the illustrated non-limiting example, the plurality of cuts 20 can extend along between about 80% and about 95% of the entire length $L_0$ of the tubular body 12. In the illustrated non-limiting example, the plurality of cuts 20 extend along at least a portion of the circumference of the tubular body 12. For example, the plurality of cuts 20 can extend along at least 50% of the circumference of the tubular body 12. According to some non-limiting examples, the plurality of cuts 20 can extend along between about 50% and about 100% of the circumference of the tubular body 12. According to the illustrated non-limiting example, the plurality of cuts 20 can extend along between about 90% and about 100% of the circumference of the tubular body 12.

The length $L_0$ of the tubular body 12 can be defined as an initial length between a first end 21 and an opposing send end 23 of the tubular body 12 when the tubular body 12 is in the retracted position (FIG. 2). According to some non-limiting examples, the length $L_0$ can be between about 0.1 cm and about 40 cm. According to other non-limiting examples, the length $L_0$ can be between about 1 cm and about 20 cm. According to yet further non-limiting examples, the length $L_0$ can be between about 1 cm and about 15 cm. According to the illustrated non-limiting example, the length $L_0$ is about 8 cm.

The tubular body 12 can also define a nominal outer diameter D, defined as an initial diameter of the outer shell 16 when the tubular body 12 is in the retracted position (FIG. 2). According to some non-limiting examples, the diameter D can be between about 1 mm and about 100 mm. According to other non-limiting examples, the diameter D can be between about 1 mm and about 50 mm. According to yet further non-limiting examples, the diameter D can be between about 1 mm and about 25 mm. According to the illustrated non-limiting example, the diameter D is about 12.5 mm.

When the tubular body 12 is elongated from the retracted position to the extended position, the tubular body 12 can define an elongated length $L_E$ (FIG. 1) that is greater relative to the initial length $L_0$. According to some non-limiting examples, the elongated length $L_E$ can be between about 1% and about 100% greater than the initial length $L_0$. According to other non-limiting examples, the elongated length $L_E$ can be between about 10% and about 80% greater than the initial length $L_0$. According to yet further non-limiting examples, the elongated length $L_E$ can be between about 15% and about 40% greater than the initial length $L_0$. According to the illustrated non-limiting example, the elongated length $L_E$ is about 30% greater than the initial length $L_0$.

The plurality of cuts 20 can be configured to form a kirigami-inspired pattern configured to undergo a shape change when stress is axially applied along the outer shell 16. via the actuator 18. The at least one cut 20 can form at least one projection element 22. In the illustrated non-limiting example, the series of patterned cuts 20 can form a plurality of projection elements 22 (e.g., needles). When the tubular body 12 of the stent 10 is in a retracted position (FIG. 2), the projection elements 22 are substantially planar with the outer shell 16 and undeformed. When the tubular body 12 of the stent 10 is elongated (e.g., via the actuator 18) from the retracted position towards the extended position (FIG. 1), the projection elements 22 become deformed and deploy to extend radially outward from the outer shell (e.g., relative to the central axis 14).

For example, as will be described, the outer shell 16 can be configured to automatically respond to strain applied in a direction along the central axis 14. That is, the series of patterned cuts 20 form a surface on the outer shell 16 that buckles in response to applied axial strain to form a plurality of projection elements from that cut surface. In the illustrated non-limiting examples, the actuator 18 is configured to apply the axial strain, and that axial strain results in stress within the outer shell 16 that causes the projection elements 22 to extend outwards from an orientation in which the projection elements form a substantially uniform (e.g., flat) cylindrical surface, into an orientation in which the projection elements deploy radially outwards relative to the central axis 14. According to some non-limiting examples, the magnitude of applied axial strain to the outer shell 16 can correspond to a magnitude of radial extension of the projection elements 22. That is, owing to the pattern of cuts 20 formed in the outer shell 16, a surface is provided that transforms in a radial direction in response to strain applied in an axial direction.

Figure 3:
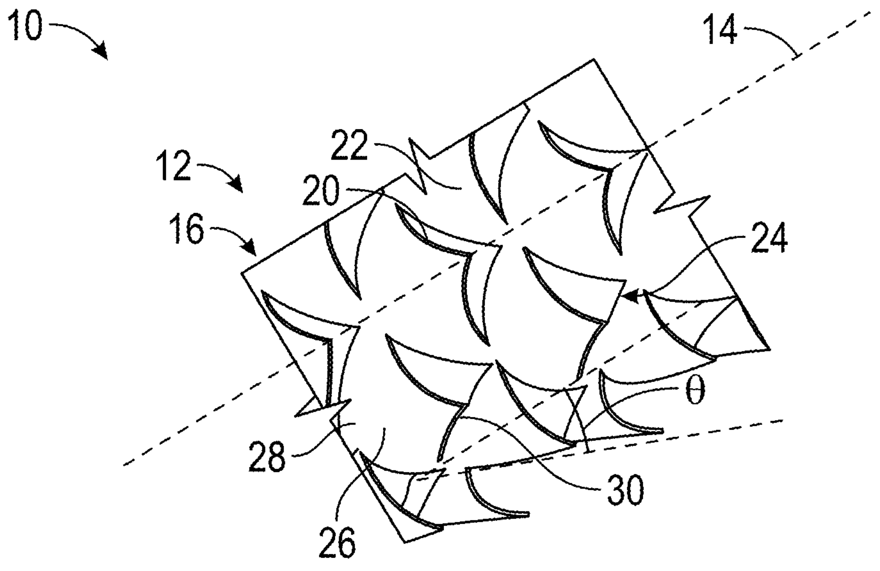
FIG. 3 illustrates a perspective detail view of denticle-like projection elements of the kirigami-inspired stent of FIG. 1 in a deployed position.
Figure 4:
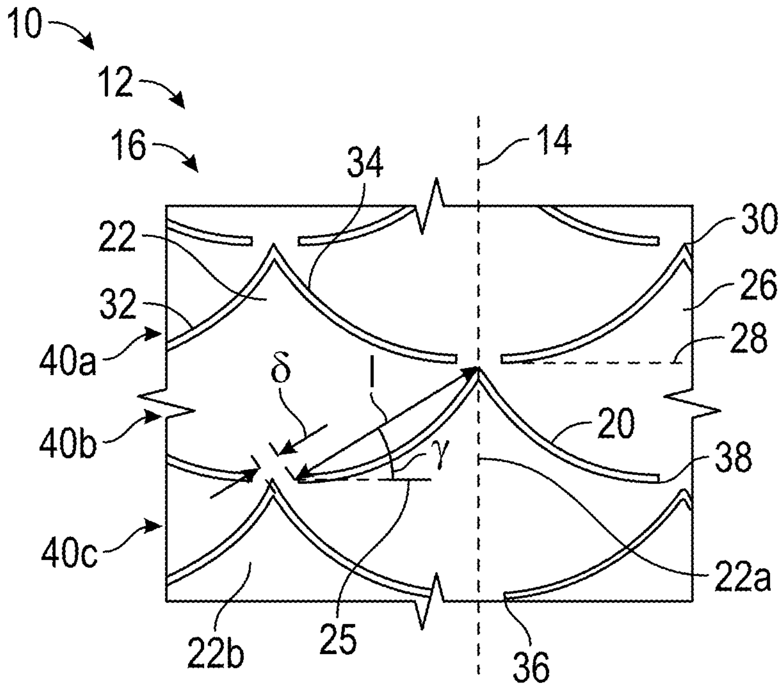
FIG. 4 illustrates a plan view of a pattern of cuts forming the denticle-like projection elements of the kirigami-inspired stent of FIG. 2 in a stowed position.

Referring now to FIGS. 3 and 4, with the tubular body 12 in an extended position, the projection elements 22 can deploy from an undeformed state (FIG. 4) to a deformed state (FIG. 3). In a deformed state, the projection elements 22 form denticle-like needles. In the illustrated non-limiting example, the projection elements 22 define a convex three-dimensional surface forming a barb shaped needle. The projection elements 22, when deployed to the deformed state, reveal a plurality of openings 24 in the outer shell 16. The plurality of openings 24 extend through the outer shell 16 and into the lumen 17.

With particular reference to FIG. 3, with the projection elements 22 in a deployed position (with the tubular body 12 in the extended position), the protruding projection elements 22 can provide radial expansion up to 80% of the stent diameter (e.g., up to 60%, 40%, etc.). In the illustrated non-limiting example, the projection elements 22 can define a needle angle θ. The needle angle θ can be defined as the angle of a surface 26 of the projection element 22, formed between a base 28 and a needle tip 30, relative to the central axis 14 of the tubular body. According to some non-limiting examples, the projection elements 22 can define a needle angle θ between about 0 degrees and about 90 degrees. According to other non-limiting examples, the projection elements 22 can define a needle angle θ between about 5 degrees and about 60 degrees. According to yet further non-limiting examples, the projection elements 22 can define a needle angle θ between about 10 degrees and about 40 degrees. According to the illustrated non-limiting example, the projection elements 22 define a needle angle θ of about 20 degrees.

Referring now to FIG. 4, illustrating the projection elements 22 in an undeformed state (e.g., in a stowed state, with the tubular body in the retracted position), the cuts 20 can be configured as a pattern of denticle-like cuts. For example, each individual projection element 22 among the plurality of projection elements 22 formed by the pattern of cuts 20 can define a triangular shaped cutting edge, with first and second edges 32, 34 of the triangular shape being formed by a continuous cut 20, and the base 28 (illustrated in FIG. 4 as a broken line) being formed by an uncut portion. In the illustrated non-limiting, the projection elements 22 define a circular triangle. That is, the first and second edges 32, 34 of each projection element 22 define an arcuate shape. In the illustrated embodiment, the first and second edges 32, 34 of the projection element 22 define a convex arcuate shape. The arcuate shape of the first and second edges 32, 34 can define a radius of curvature between being a straight line and about a 100 mm radius. According to some non-limiting examples, the radius of curvature can be between about 1 mm and about 60 mm. According to other non-limiting examples, the radius of curvature can be between about 1 mm and about 40 mm. According to yet further non-limiting examples, the radius of curvature can be between about 1 mm and about 20 mm. According to the illustrated non-limiting example, the radius of curvature is about 10 mm.

The patterned cuts 20 forming the projection elements 22 can be characterized by a needle length l, hinge length δ, and cut angle γ. The needle length l can be described as a characteristic length of the patterned cut 20 and can be considered as a length of the needle formed by the projection element 22. The needle length l can be defined by a distance between the needle tip 30 of the projection element 22 and either one of a first distal end 36 of the first edge 32 or a second distal end 38 of the second edge 34 (i.e., distal ends of the cut 20). According to some non-limiting examples, the projection elements 22 can define a needle length l between about 0.1 mm and about 60 mm. According to other non-limiting examples, the projection elements 22 can define a needle length l between about 1 mm and about 30 mm. According to yet further non-limiting examples, the projection elements 22 can define a needle length l between about 1 mm and about 15 mm. According to the illustrated non-limiting example, the projection elements 22 define a needle length l of about 10 mm.

The hinge length δ can be described as the width of ligaments forming an interstitial spacing separating adjacent cuts 20. The hinge length δ can be defined by a distance between the needle tip 30 of a first projection element 22*a* and either one of the first distal end 36 or the second distal end 38 of a second, adjacent projection element 22*b*. According to some non-limiting examples, the cuts 20 can define a hinge length δ between about 0.1 mm and about 10 mm. According to other non-limiting examples, the cuts 20 can define a hinge length δ between about 0.1 mm and about 5 mm. According to yet further non-limiting examples, the cuts 20 can define a hinge length δ between about 0.1 mm and about 2 mm.

The cut angle γ can be described as the angle of the cut 20 forming either one of the first and second edges 32, 34 of the projection element 22 relative to a plane 25 intersecting and orthogonal to the central axis 14. According to some non-limiting examples, the cuts 20 can define a cut angle γ between about 0 degrees and about 90 degrees. According to other non-limiting examples, the cuts 20 can define a cut angle γ between about 5 degrees and about 45 degrees. According to yet further non-limiting examples, the cuts 20 can define a cut angle γ between about 10 degrees and about 45 degrees. According to the illustrated non-limiting example, the cuts 20 define a cut angle γ of about 30 degrees.

Referring still to FIG. 4, a dimensionless ratio δ/l can be defined for a given pattern of cuts 20, the dimensionless ratio δ/l can correlate to a magnitude of pop-out deformation (e.g., a magnitude of needle angle θ, a magnitude of convex surface deformation in the projection elements 22, etc.) upon elongation of the tubular body 12. According to some non-limiting examples, the cuts 20 can define a dimensionless ratio δ/l between 0 and 1. According to other non-limiting examples, the cuts 20 can define a dimensionless ratio δ/l between 0 and about 0.5. According to yet further non-limiting examples, the cuts 20 can define a dimensionless ratio δ/l between 0 and about 0.2. According to the illustrated non-limiting example, the cuts 20 define a dimensionless ratio δ/l of about 0.13.

The cuts 20 forming the projection elements 22 can be evenly (e.g., periodically) circumferentially spaced around the outer shell 16 (see, e.g., FIG. 1). According to the illustrated non-limiting example, a plurality of rows of circumferentially spaced cuts 20 are arranged along the axial length of the outer shell 16. As best illustrated in FIG. 4, a first row 40*a* of circumferentially spaced cuts 20 can be rotationally offset from a second, adjacent row 40*b* of circumferentially spaced cuts 20. In the illustrated non-limiting example, the rotational offset between adjacent rows 40*a*, 40*b* of circumferentially spaced cuts 20 can be such that a needle tip 30 of a projection element 22 within the second row 40*b* is in rotational alignment between distal ends 36, 38 of two adjacent projection elements 22 within the first row 40*a*. That is, the rotational offset between adjacent rows 40*a*, 40*b* can be such that the needle tip 30 of a projection element 22 within a row 40 is rotationally aligned with a needle tip 30 of a projection element 22 in every other row. For example, the needle tips 30 in the first row 40*a* can be rotationally aligned with the needle tips 30 in a third row 40*c*, with the second row 40*b* being both between and directly adjacent to each of the first and third rows 40*a*, 40*c*.

The outer shell 16 of the tubular body 12 of the stent 10 can be formed from a thin sheet of material. According to some non-limiting examples, the outer shell 16 is formed of an elastomeric material (e.g., plastic, a polyester plastic, etc.). According to other non-limiting examples, the outer shell 16 can be formed of a metal, a polymer, or a composite. In some non-limiting examples, the outer shell 16 can be formed of rigid, thin sheets of steel, nitinol, or plastic and the "elasticity" of the material can be provided by the pattern of cuts 20. In other non-limiting examples, the outer shell 16 can be formed of soft flexible materials such as rubbers. In yet further non-limiting examples, the outer shell 16 can be formed of soluble polymers. The material of the outer shell 16 can have a shape memory, thereby allowing the projection elements 22 of the outer shell 16 to repeatedly transition between the deformed and undeformed states. According to some non-limiting examples, the outer shell 16 can define a wall thickness between about 0.01 mm and about 2 mm. According to other non-limiting examples, the wall thickness can be between about 0.05 mm and about 1 mm. According to yet further non-limiting examples, the wall thickness can be between about 0.05 mm and about 0.5 mm. According to the illustrated non-limiting example, wall thickness is about 0.13 mm.

Figure 5:
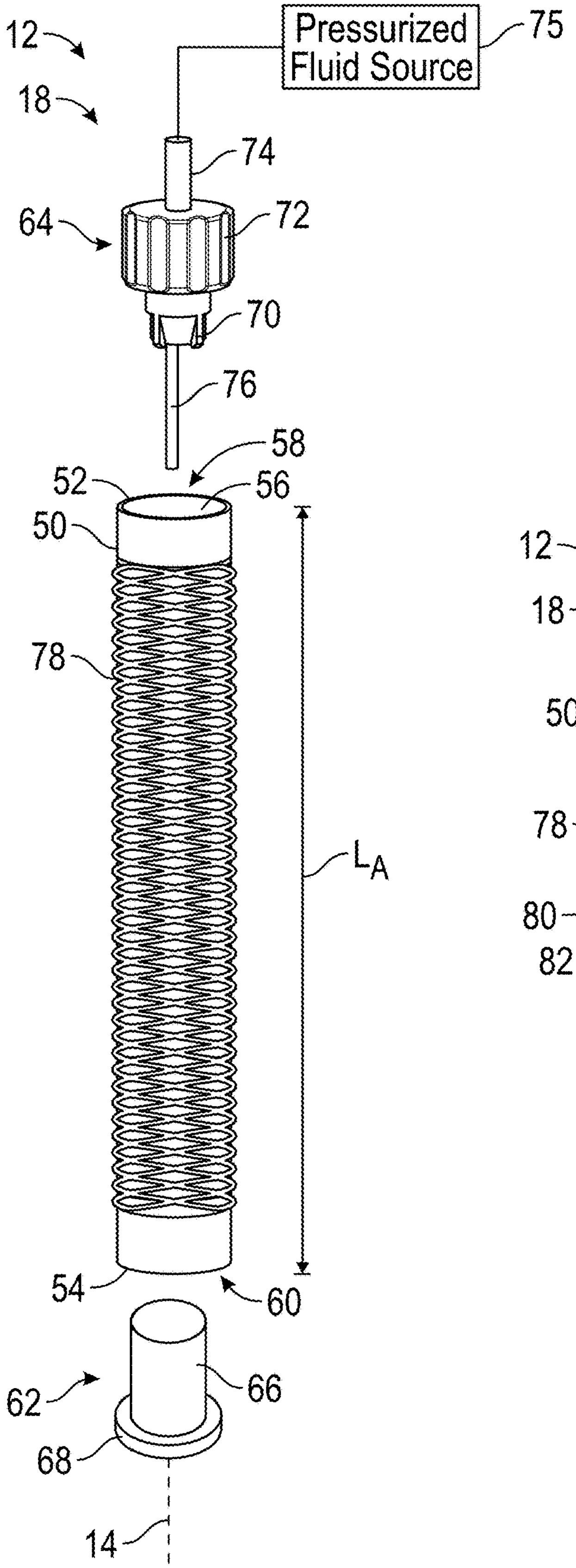
FIG. 5 illustrates a perspective exploded view of an actuator for the kirigami-inspired stent of FIG. 2.

As previously described herein, the outer shell 16 of the tubular body 12 can define a lumen (e.g., a hollow core) configured to receive an actuator 18. FIG. 5 illustrates one non-limiting example of the actuator 18 configured to actuate the stent 10 between the extended and retracted positions. In the illustrated non-limiting example, the actuator 18 is a soft fluid-powered actuator (e.g., a pneumatic actuator), although other forms linear actuators are also possible. For example, the actuator can be an electric, hydraulic, mechanical, or magnetic actuator. According to other non-limiting examples, the actuator can be any form of actuator configured to provide linear motion, such as a plunger or rod manually controlled by a physician (e.g., a mechanical actuator), a piezoelectric actuator, a motor-powered actuator (e.g., a stepper motor). The actuator 18 can include a cylindrical body 50 extending along the central axis 14 from a first actuator end 52 to a second actuator end 54 opposite the first actuator end 52. The material of the cylindrical body 50 can have a shape memory, thereby allowing the cylindrical body to repeatedly transition between the extended and retracted positions. According to some non-limiting examples, the cylindrical body is formed of an elastomeric material (e.g., silicone-based rubber, latex, etc.).

The body 50 of the actuator 18 can define a hollow tube including an interior cavity 56. According to some non-limiting examples, the body 50 can define a wall thickness between about 0.01 mm and about 5 mm. According to other non-limiting examples, the wall thickness can be between about 0.05 mm and about 3 mm. According to yet further non-limiting examples, the wall thickness can be between about 0.05 mm and about 2 mm. According to the illustrated non-limiting example, wall thickness is about 1.5 mm.

The interior cavity 56 can extend through the body 50 between the first actuator end 52 and the second actuator end 54. In the illustrated non-limiting example, the interior cavity 56 forms a first opening 58 at the first actuator end 52 and a second opening 60 at the second actuator end 54. The actuator can also include a plug 62 and a cap 64. The plug 62 can be coupled at the second actuator end 54 of the actuator 18 to enclose the second opening 60. The plug 62 includes a plug boss 66 and a plug flange 68 at a distal end thereof extending radially outward from the plug boss 66. The plug boss can be configured to be received within the interior cavity 56 of the body 50. The plug flange 68 can be configured to abut the second actuator end 54 of the body 50, when the actuator 18 is in an assembled state (see, e.g., FIG. 2). According to some non-limiting examples, the plug 62 can define a press-fit between the plug boss 66 and the interior cavity 56 of the body 50 to form a fluid impervious seal. According to the illustrated non-limiting example, the plug 62 can be formed of an elastomeric material or a hard material (e.g., a plastic).

The cap 64 can be coupled at the first actuator end 52 of the actuator 18 to enclose the first opening 58. The body 50, plug 62, and cap 64 together define and enclose the interior cavity 56. The cap 64 can include a cap boss 70 and a cap flange 72 at a distal end thereof and extending radially outward from the cap boss 70. The cap boss 70 can be configured to be received within the first opening 58. The cap flange 72 can be configured to abut the first actuator end 52 of the body 50, when the actuator 18 is in the assembled state, to form a fluid impervious seal with the body 50. According to the illustrated non-limiting example, the cap 64 can be formed of an elastomeric material or a hard material (e.g., a plastic). According to some non-limiting examples, the cap 64 can include a nylon plastic quick-turn plug.

The cap 64 can include an inlet port 74 and a fluid passage 76 in fluid communication with the inlet port 74. The fluid passage 76 is configured to provide fluid communication between the inlet port 74 and the interior cavity of the actuator 18. The inlet port 74 can extend axially outward from the first end 21 of the outer shell 16 of the stent 10 (see FIG. 2). The inlet port 74 can be configured to be coupled to a pressurized fluid source 75 (e.g., compressed air), thereby allowing fluid from the pressurized fluid source to enter the interior cavity 56 and extend or retract the actuator 18. In the illustrated non-limiting example, the fluid passage 76 can be configured as a blunt needle (e.g., a 20G blunt needle). In the illustrated non-limiting example, the inlet port 74 can be configured as a barbed fitting.

Figure 6:
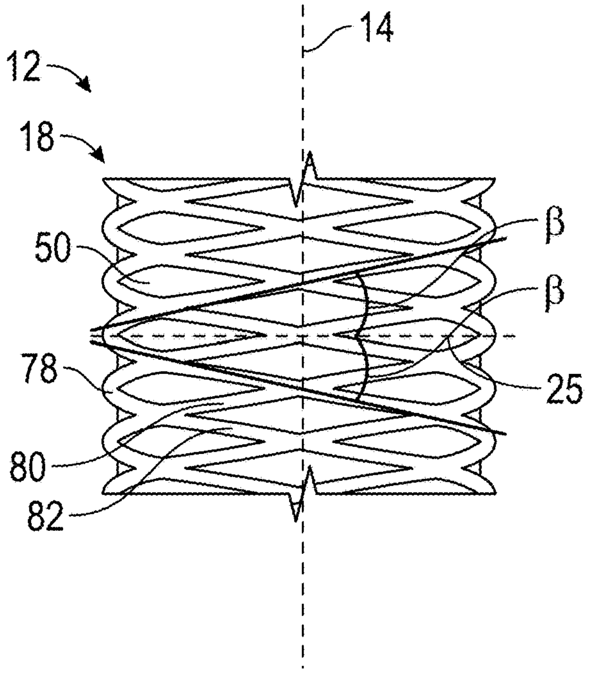
FIG. 6 illustrates a perspective detailed view of a fiber reinforcement for the actuator of FIG. 5.

Referring now to FIGS. 5 and 6, the body 50 can include a fiber reinforcement 78 configured to constrain the deformation of the actuator 18 in the radial direction. Restricting the radial deformation can enable an increased performance in the axial direction forming an extensional actuator. The fiber reinforcement 78 can extends along at least a portion of the axial length $L_A$ of the actuator 18. For example, the fiber reinforcement 78 can extend along at least 50% of the length $L_A$ of the body 50. According to some non-limiting examples, the fiber reinforcement 78 can extend along between about 50% and about 100% of the length $L_A$ of the body 50. According to the illustrated non-limiting example, the fiber reinforcement 78 can extend along between about 80% and about 95% of the length $L_A$ of the body 50. According to some non-limiting examples, the fiber reinforcement 78 can be formed of Kevlar fibers. According to other non-limiting examples, the fiber reinforcement 78 can be formed of metal fibers. According to some non-limiting examples, the body 50 can be reinforced using rigid, circular rings along the length of the body 50 of the actuator 18. For example, a plurality of rigid (e.g., steel, nitinol, or plastic) circular rings can be arranged and axially separated along the length of the body 50 to prevent radial expansion of the body 50 and allow for axial extension.

As best illustrated in FIG. 6, the fiber reinforcement 78 can include strands of fibers arranged in a helical pattern. The fiber reinforcement 78 can include a first helical strand 80 wrapped around the body 50 in a first axial direction and a second helical strand 82 wrapped around the body 50 in a second axial direction opposite the first direction, thereby forming the helical pattern. The helical pattern can be defined by a characteristic fiber angle β, as measured when the actuator 18 is in a retracted position. The fiber angle β can be described as the angle of the wrapping of either one of the first and second strands 80, 82 relative to the plane 25 intersecting and orthogonal to the central axis 14. According to some non-limiting examples, the helical pattern can define a fiber angle β between about 1 degrees and about 60 degrees. According to other non-limiting examples, the helical pattern can define a fiber angle β between about 5 degrees and about 45 degrees. According to yet further non-limiting examples, the helical pattern can define a fiber angle β between about 5 degrees and about 30 degrees. According to the illustrated non-limiting example, the helical pattern defines a fiber angle β of about 10 degrees.

Figure 7:
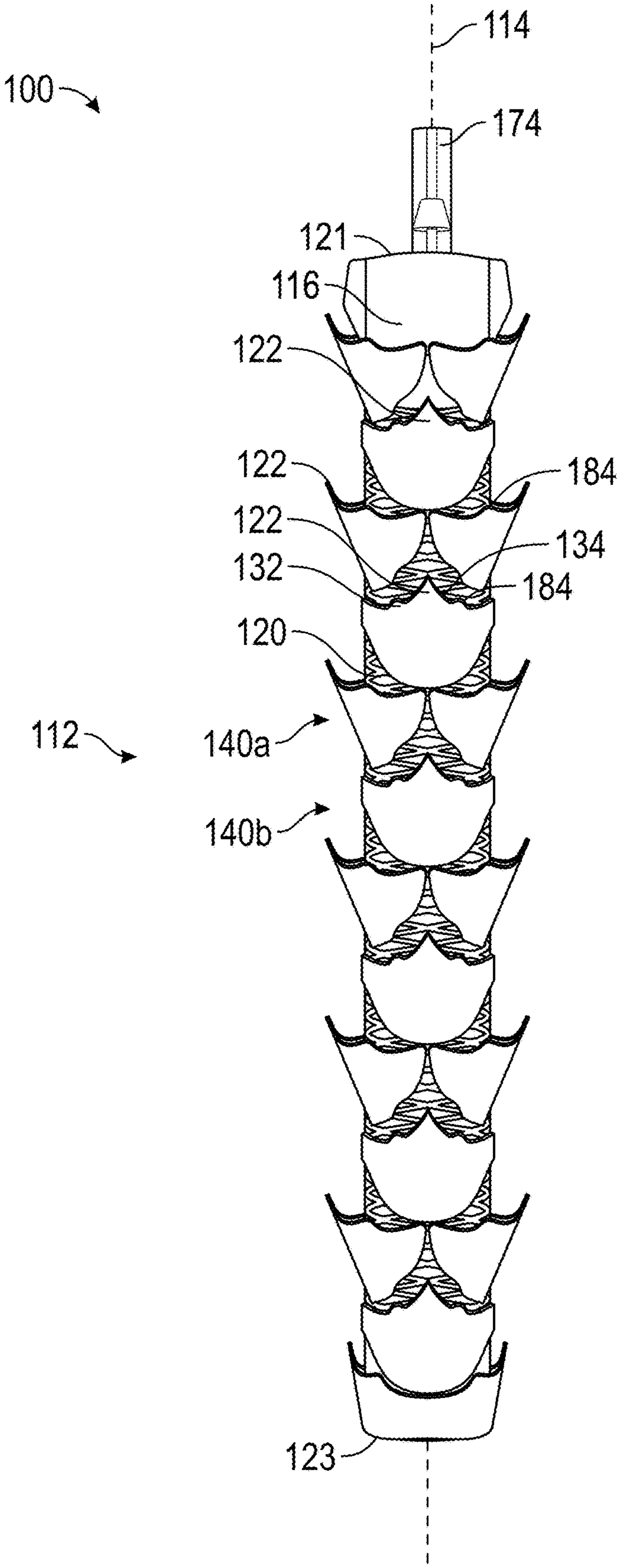
FIG. 7 illustrates a perspective view of another non-limiting example of a kirigami-inspired stent in an extended position according to another aspect of the present disclosure.

FIG. 7 illustrates another non limiting example of a stent 100. In the illustrated non-limiting example, unless otherwise described below or illustrated in the figure, like elements are labeled with like reference numerals in the 100's (e.g., projection element 22 is labeled as projection element 122). The stent 100 of FIG. 7 is substantially similar to that of the stent 10 of FIG. 1, as such, only aspects that differ from those previously described will be discussed. For example, in the illustrated non-limiting example, a first row 140*a* of circumferentially spaced cuts 120 is rotationally offset from a second, adjacent row 140*b* of circumferentially spaced cuts 120 by approximately 180 degrees.

Figure 8:
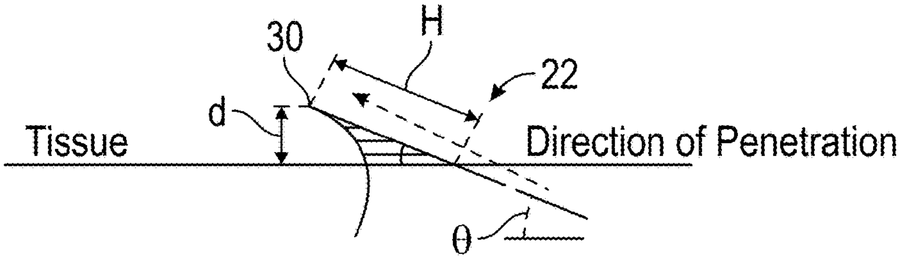
FIG. 8 illustrates a schematic of a penetration depth of a projection element of the kirigami-inspired stents.

The projection elements 122 illustrated in FIG. 7 can include one or more protrusions 184 located along the first and second edges 132, 134. The protrusions 184 can be configured to control a penetration depth of the projection elements 122 (e.g., needles) into the tissue of a subject. As best illustrated in FIG. 8, the penetration depth of projection elements (e.g., projection elements 22, 122, etc.) can be characterized by the effective needle length H and the penetration depth d. The effective needle length H can be defined by a distance between the needle tip 30 of the projection element 22 and either one of a base 28 of the projection element (e.g., projection element 22 of FIG. 1) or a protrusion 184 of the projection element (e.g., projection element 122 of FIG. 7). The penetration depth d can be defined as the radial distance the needle tip of a projection element has penetrated into the tissue of a subject.

Figure 9:
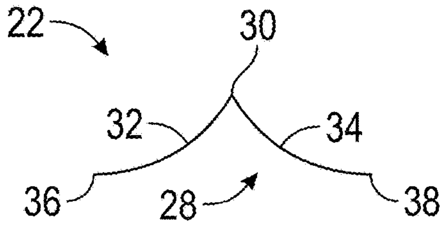
FIG. 9 illustrates a schematic of an exemplary cut forming the projection elements of the kirigami-inspired stent of FIG. 1.
Figure 10:
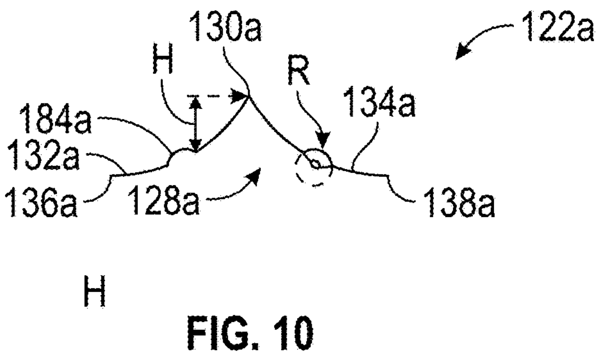
FIG. 10 illustrates a schematic of an exemplary cut forming the projection elements akin to the kirigami-inspired stent of FIG. 7.
Figure 11:
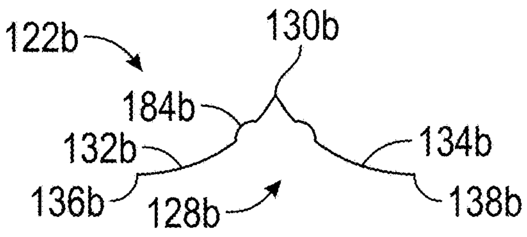
FIG. 11 illustrates a schematic of another exemplary cut forming the projection elements akin to the kirigami-inspired stent of FIG. 7.
Figure 12:
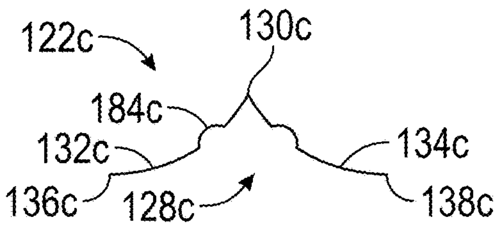
FIG. 12 illustrates a schematic of yet another exemplary cut forming the projection elements akin to the kirigami-inspired stent of FIG. 7.

FIG. 9 illustrates one non-limiting example of a projection element 22, such as those illustrated in the stent 10 of FIGS. 1-4. In the illustrated non-limiting example, the first and second edges 32, 34 of the projection element 22 lacks any protrusions. FIGS. 10-12 illustrate non-limiting examples of protrusions 184*a*, 184*b*, 184*c*, such as those illustrated in the stent 100 of FIG. 7, along the first and second edges 132, 134 of the projection elements 122 defining various effective needle lengths H (see FIG. 10). For example, the protrusions 184 (e.g., 184*a*, 184*b*, 184*c*) can be arranged at a distance away from the needle tip 130 that is between about 10% to about 95% of the total length of the projection element. According to some non-limiting examples, the protrusions 184 can be arranged at a distance away from the needle tip 130 that is between about 30% to about 95% of the total length of the projection element.

As illustrated in FIG. 10, each of the first and second edges 132*a*, 134*a* of the projection element 122*a* include a round, dimple-shaped protrusion 184*a*. The protrusion 184*a* can define a radius R. According to some non-limiting examples, the radius R can be between about 0.1 mm and about 5 mm. According to other non-limiting examples, the radius R can be between about 0.5 mm and about 2.5 mm. According to the illustrated non-limiting examples illustrated in FIGS. 10-12, the radius R is about 1.5 mm.

Figure 13:
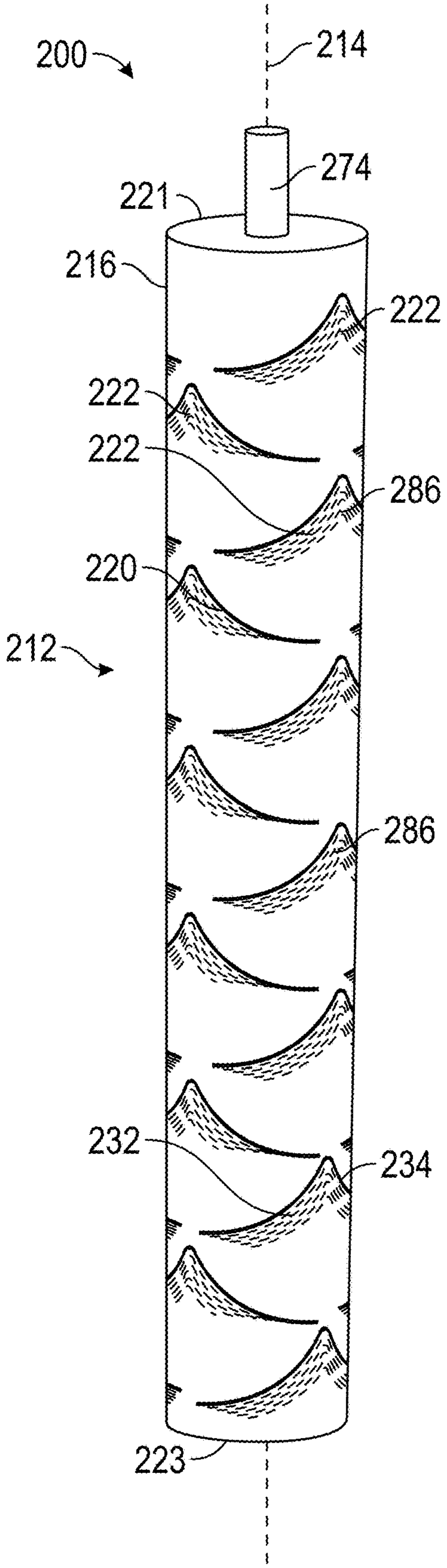
FIG. 13 illustrates a perspective view of another non-limiting example of a kirigami-inspired stent in a retracted position according to another aspect of the present disclosure.

FIG. 13 illustrates another non limiting example of a stent 200. In the illustrated non-limiting example, unless otherwise described below or illustrated in the figure, like elements are labeled with like reference numerals in the 200's (e.g., projection element 22 is labeled as projection element 222). The stent 200 of FIG. 13 is substantially similar to that of the stent 10 of FIG. 1, as such, only aspects that differ from those previously described will be discussed. In the illustrated non-limiting example, the plurality of projection elements 222 can include one or more etched striations 286 (e.g., lines) formed into the outer surface of the outer shell 216.

Figure 14:
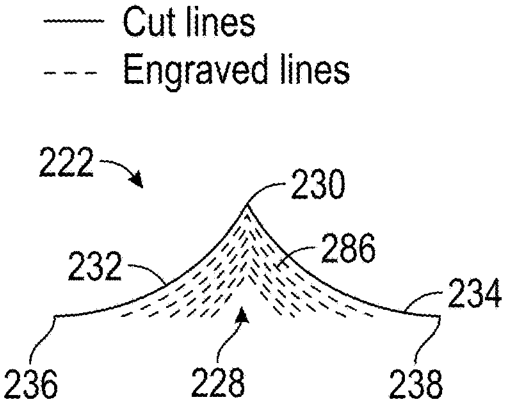
FIG. 14 illustrates a schematic of the projection elements of the kirigami-inspired stent of FIG. 13 including etched striations according to one aspect of the present disclosure.

As best illustrated in FIG. 14, the projection element 222 can include a plurality of striations 286. The striations 286 can be configured to provide a more robust surface for the loading of therapeutic agents or coatings onto the projection elements. For example, the striations 286 can improve adhesion between the surface of the outer shell 216 and a therapeutic coating or surface coating layer. The plurality of striations 286 can be shaped similar to the triangular projection element 222, such that the lines formed by the striations 286 are substantially parallel (e.g., evenly offset from) the first and second edges 232, 234 of the projection element 222. According to some non-limiting examples, the projection element 222 can include between about 1 and about 20 striations 286. According to some non-limiting examples, the projection element 222 can include between about 1 and about 10 striations 286. In the illustrated non-limiting example, the projection element 222 includes six striations 286. The striations 286 can be evenly separated (e.g., offset from) an adjacent striation. For example, the pattern of striations 286 can define a spacing between adjacent striations 286 that is between about 0.05 mm and about 2 mm. According to some non-limiting examples, the pattern of striations 286 can define a spacing between adjacent striations 286 that is between about 0.1 mm and about 1 mm. According to the illustrated non-limiting example, the pattern of striations 286 defines a spacing between adjacent striations 286 that is about 0.5 mm.

Figure 15:
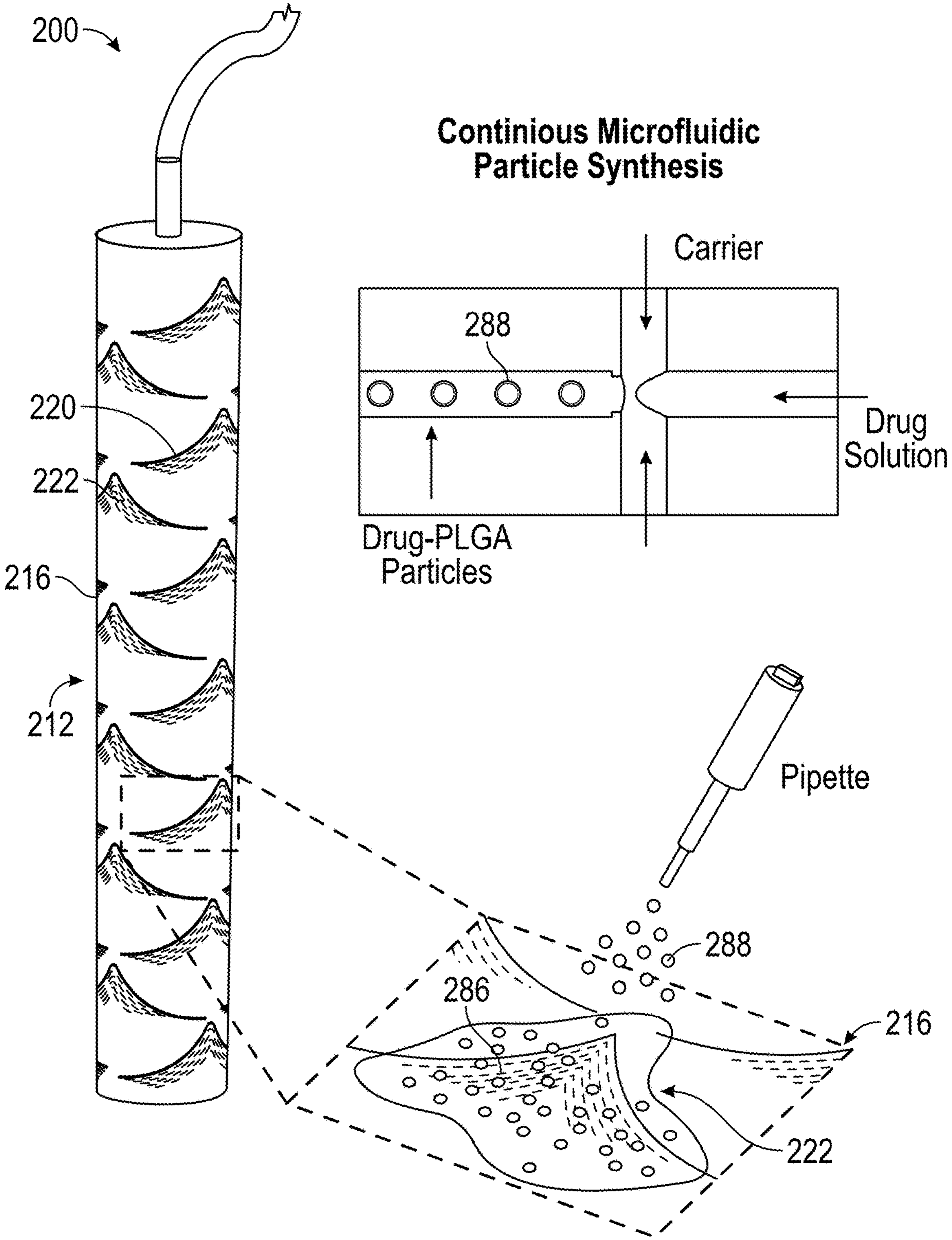
FIG. 15 illustrates an exemplary method of loading a therapeutic agent onto a kirigami-inspired stent to produce a drug eluting stent.

Referring now to FIG. 15, stents (e.g., stent 10, 100, 200, etc.) can be configured as drug eluting stents. For example, at least a portion of the stent can be coated in a therapeutic agent. According to one non-limiting example, the projection elements 222 of the stent 200 can be coated with a therapeutic agent in the form of drug particles 288 (e.g., drug-loaded polymeric particles) to enable the local delivery of therapeutics to submucosal tissues through circumferential injections within the tubular structure of the GI tract or trachea of a subject. According to one non-limiting example, the projection elements 222 (e.g., needles) of the stent 200 can be coated by pipetting a therapeutic agent via a pipet 290. The therapeutic agent can be entrapped or concentrated on the projection elements 222 via the striations 286 thereon. According to some non-limiting examples, the stent 200 can include polymeric sacrificial layers surrounding the stent 200 that are configured to protect the drug-coated particles, which can also increase drug loading capacity.

According to one non-limiting example, the therapeutic agent can include an anti-inflammatory drug (e.g., budesonide, prednisone, colchicine, resveratol, etc.), and anti-proliferative drugs (e.g., paclitaxel, everolimus, sirolimus, among other-limus agents, etc.), for delivery to walls of the GI tract or trachea. Budesonide, for example, is an anti-inflammatory drug commonly used to treat inflammatory bowel disease and eosinophilic GI disorders. In the illustrated embodiment, budesonide can be encapsulated into poly lactic-co-glycolic acid ("PLGA") microparticles using a continuous microfluidic droplet generation method (generally illustrated in FIG. 15). According to some non-limiting examples, the drug particles 228 can be formulated with various concentrations of the therapeutic agent. For example, budesonide loaded PLGA particles can be used with 75, 100, or 125 mg/ml concentration of budesonide (denoted by BUD 75, BUD 100, and BUD 125, respectively). Additionally, a concentration (e.g., 100 mg/ml) of fluorescent budesonide-PLGA particles (denoted BUD 100F) can be added via a fluorescent agent configured to allow for confirmation of the therapeutic agent delivery using various forms of imagery.

In the above description, reference is made to various dimensions, parameters, and characteristics of the stent 10 and its components. It is to be understood that these components can be sized based on the intended application. For example, within the GI tract, stents 10 can be configured for placement within the stomach, esophagus, colon, small intestine, or large intestine. Dimensions and parameters of the stents 10 can be chosen based on the application or dimensions of the tubular structures of the GI tract or trachea for a given subject. For example, depending on the target position of deployment of the stent, a desired diameter and length of the stent may be determined (i.e., based on a diameter and length of the target position). Based on a determined diameter and length of the stent, the pattern of cuts 20 (e.g., needle, length, cut angle, hinge length, etc.) can be determined such that the resulting kirigami stent 10 expands to reach a desired penetration depth. For example, hinge length can be determined or calculated based on needle length, cut angle, thickness, and/or material of the outer shell 16 to provide the pop-up deployment motion of the projection elements 22.

Methods of Inserting/Removing a Kirigami-Inspired Stent

Figure 16:
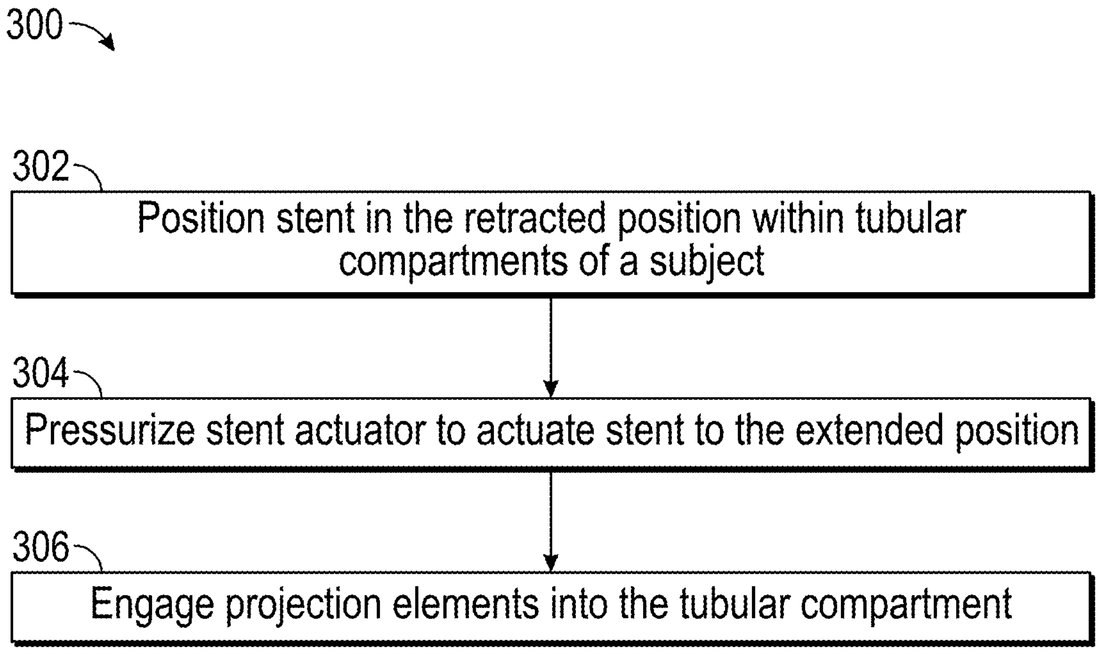
FIG. 16 illustrates a flow diagram of a method of inserting and removing a kirigami-inspired stent according to one aspect of the present disclosure.

Referring now to FIGS. 1, 2, and 16, the kirigami-inspired stents 10 are capable of reversible shape transformation from a retracted position (FIG. 2), in which the projection elements 22 are in a flat, undeformed state resulting in a smooth outer surface of the outer shell 16, to an extended position (FIG. 1), in which the projection elements 22 are transitioned into a deformed state and configured to provide popped-up needles configured for injections into a tissue of a subject. With the tubular body 12 of the stent 10 in the retracted position, the stent 10 can be delivered and removed from tubular structures within the subject (e.g., GI tract or trachea). With the tubular body 12 of the stent 10 in the extended position, the projection elements 22 (e.g., needles) of the stent 10 can deliver circumferential injections to pierce the tissue of the subject, and according to some non-limiting examples, deliver a therapeutic agent into the injection sites. Thus, the stent systems described herein can provide facile, in vivo delivery, robust deployment, and safe removal of a stent configured for injections, and according to some non-limiting examples, providing a drug releasing system. It is to be understood that the following method 300 can be applied to each of the stents described herein (e.g., stent 10, 100, 200). In the following description reference will be made to the stent 10 of FIGS. 1-4.

Figure 18:
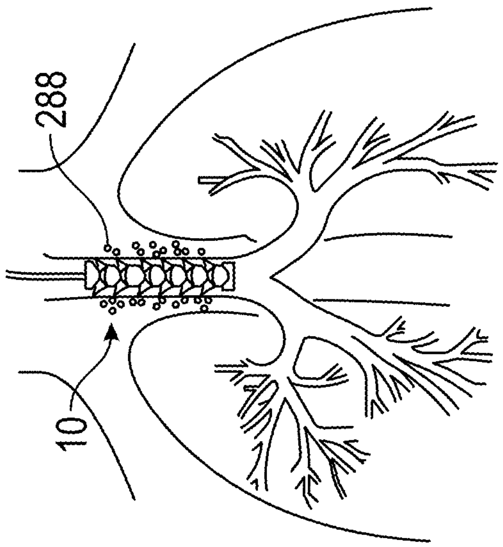
FIG. 18 illustrates an exemplary schematic of a kirigami-inspired stent inserted into a subject's trachea.
Figure 17:
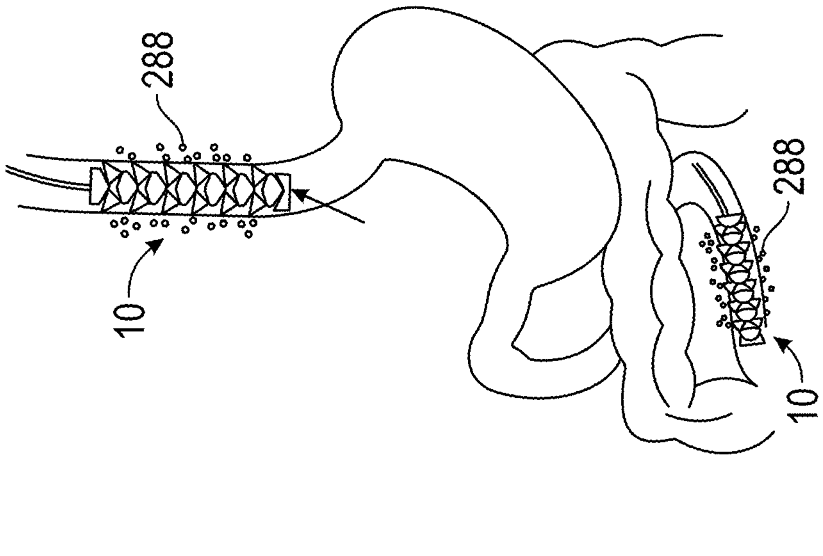
FIG. 17 illustrates an exemplary schematic of a kirigami-inspired stent inserted into different portions of a subject's GI tract.

The method can begin at 302 by inserting the stent 10 into a tubular tissue structure of a subject in a first, insertion direction (e.g., relative to the central axis 14). For example, the stent 10 can be inserted into the GI tract (FIG. 17) or the trachea (FIG. 18) by applying a pushing force to the first end of the tubular body 12 of the stent 10. During insertion, the stent 10 is in the retracted position (FIG. 2) with the actuator 18 unpressurized. According to some non-limiting examples, a tube dimensioned to receive the stent 10 therein can be inserted into the tubular structure of the subject prior to insertion of the stent 10. The tube can be configured to guide delivery of the stent 10 to a tissue site of interest.

Once the stent 10 is positioned at the tissue site of interest, the actuator 18 can be actuated 304 from the retracted position towards the extended position, thereby deploying the projection elements 22 radially outward into the deformed state. For example, the actuator 18 can be pressurized by the pressurized fluid source 75 coupled to the inlet port 74 and the actuator 18 can begin to elongate to engage the enclosed first and second ends 21, 23 of the outer shell 16 of the tubular body 12, thereby elongating the outer shell 16 and deforming the projection elements 22 to deploy radially outwards.

With the stent 10 in the extended position, the projection elements 22 can engage 306 the tissue of the subject to form a pattern of circumferential injection sites into the tissue. According to some non-limiting examples, the stent 10 can be moved in a second, removal direction by applying a pulling force to the first end of the tubular body 12 of the stent 10. By moving the stent 10 in the second direction with the projection elements 22 deployed, the projection elements can be further driven into the tissue of the subject to increase the insertion depth of the projection elements 22. For example, the projection elements 22, when deployed, generally extend from the second end 23 towards the first end 21 of the tubular body 12, owing to the needle angle θ (see, e.g., FIG. 3). Thus, movement of the stent 10 in the second direction (towards the first end 21) can drive the projection elements 22 into the tissue of the subject.

As previously described, the projection elements 22 can be loaded with a therapeutic agent (see, e.g., FIG. 9), and insertion of the projection elements 22 can be configured to deposit the therapeutic agent (e.g., in the form of drug particles 288) at the circumferential injection sites. According to some non-limiting examples, the stent can be left in place for a period of minutes, hours, or days (e.g., up to a week or more) to provide prolonged delivery of the therapeutic agent via the drug-loaded projection elements 22.

For removal of the stent 10, the stent 10 can be moved in the first direction (towards the second end 23) to remove the projection elements 22 from the tissue of the subject. With the projection elements 22 removed, the stent 10 can be actuated from the extended position towards the retracted position to stow the projection elements into the undeformed state. Once the stent 10 is in the retracted position, the stent 10 can be removed from the subject by moving the stent 10 in the second, removal direction, for example, by again applying a pulling force to the first end of the tubular body 12 of the stent 10.

Methods of Making a Kirigami-Inspired Stent

Figure 21:
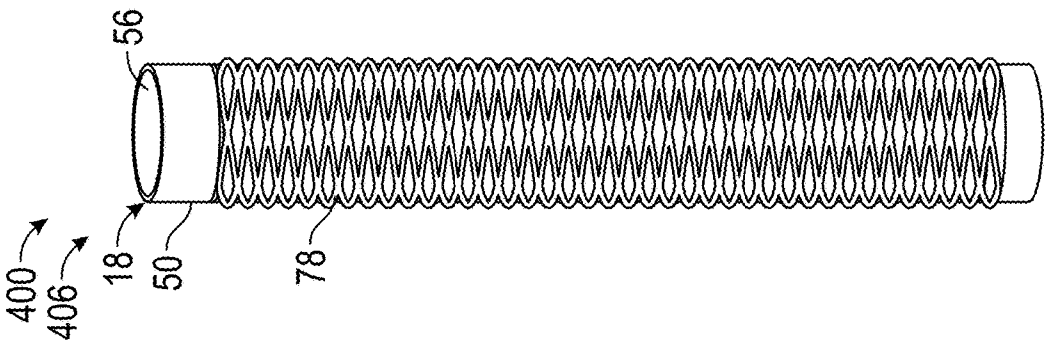
FIG. 21 illustrates a perspective view of the cast or injection molded actuator body of FIG. 20 with a fiber reinforcement wrapping.
Figure 20:
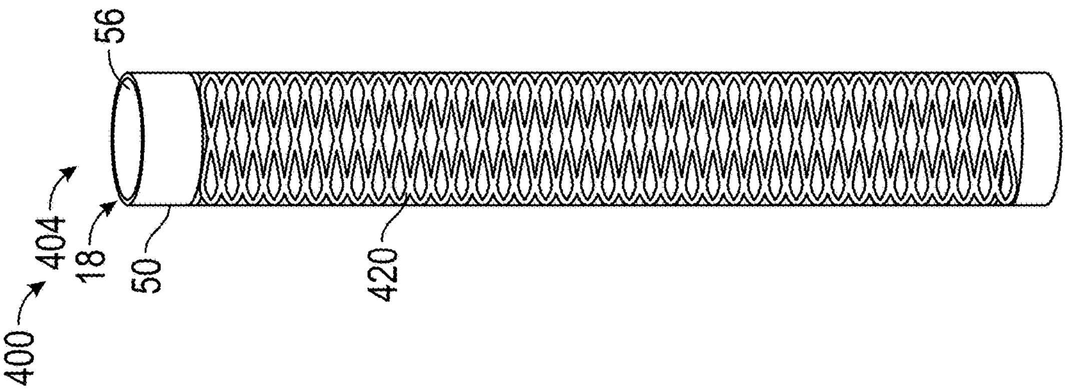
FIG. 20 illustrates a perspective view of the cast or injection molded actuator body of FIG. 19 out of the mold.
Figure 19:
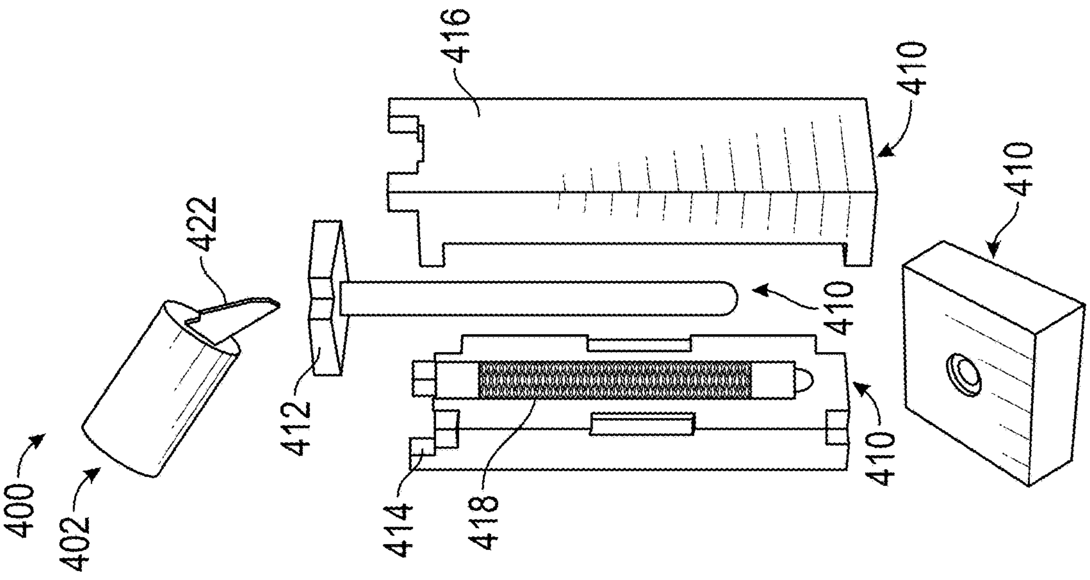
FIG. 19 illustrates a perspective view of a molding process for making a cast or injection molded actuator body.

Referring now to FIGS. 19-21, a non-limiting example of a method 400 of making the actuator 18 for the stent 10 is illustrated. It is to be understood that the following method 400 can be applied to each of the stents described herein (e.g., stent 10, 100, 200). In the following description reference will be made to the stent 10 of FIGS. 1-4. As illustrated in FIG. 19, the body 50 of the actuator 18 can be formed via a casting or injection molding process 402. The casting or injection molding process can include providing a multi-piece mold 410 (FIG. 19), including a first part 412 forming the interior cavity 56, and second and third parts 414, 416 forming the body 50. In the illustrated non-limiting example, the second and third parts 414, 416 of the mold 410 can include a pattern of helical protrusions 418 configured to form helical recesses 420 along the body 50 to receive the fiber reinforcement 78 (FIG. 20).

According to some non-limiting examples, the mold 410 can be sprayed with a releasing agent for easy demolding. Then, the elastomeric actuator body 50 and plug 62 can be cast separately using an elastomeric material (e.g., a silicone-base rubber, vinylpolysiloxane, a-silicone). According to some non-limiting examples, the elastomeric material can be a duplicating elastomer (e.g., Elite Double 8). The casted mixture can be mixed for a predetermined period of time (e.g., two minutes), placed in a vacuum for degassing, and then allowed to set at a predetermined temperature (e.g., room temperature) for a predetermined period of time (e.g., thirty minutes) to cure.

With the body 50 formed, strands of fiber reinforcement material can be wrapped 404, 406 within the helical recesses 420 along the body 50 (FIG. 21) to form the helical-patterned fiber reinforcement 78. According to some non-limiting examples, a uniform thin layer of a silicone adhesive can be applied to the outer surface of the fiber-reinforced actuator body 50 to enhance the bonding between the fiber and elastomer. The extensional actuator body 50 can then be left to cure at a predetermined temperature for a predetermined period of time (e.g., room temperature for 30 min), allowing the silicone adhesive to dry. Then, the plug 62 and the cap 64 can be coupled with the body 50 (e.g., via an adhesive) to seal the interior cavity 56 (see FIG. 5).

Figure 24:
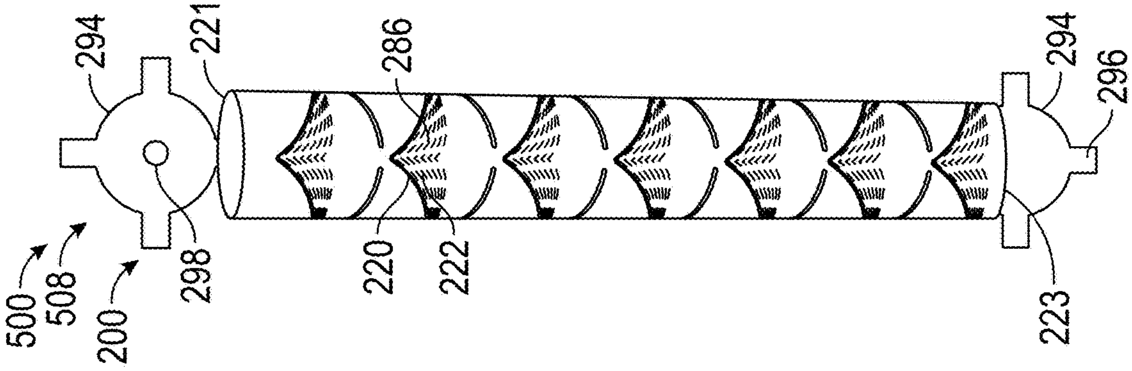
FIG. 24 illustrates a perspective view of the outer shell of FIG. 22 in an assembled state in preparation for receiving an actuator.
Figure 23:
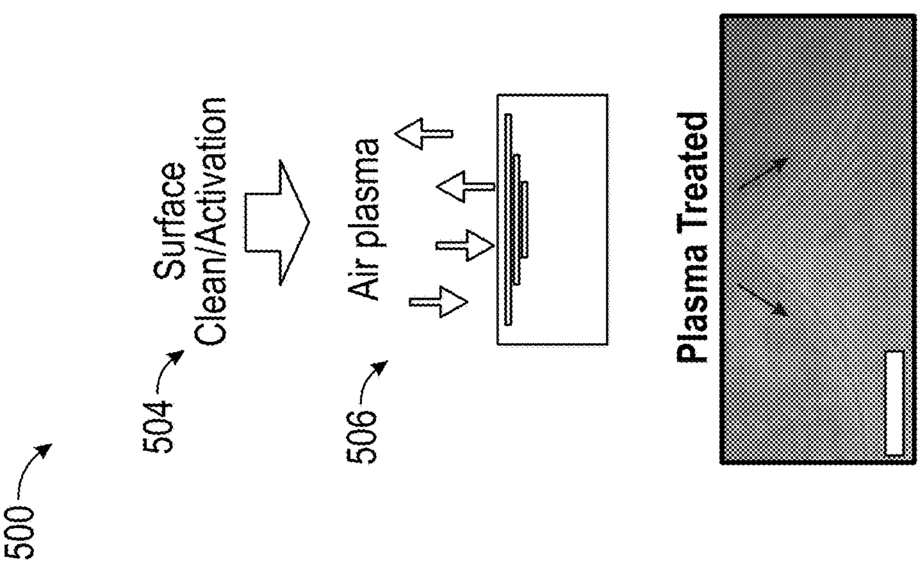
FIG. 23 illustrates a flow diagram of a surface treatment process for the outer shell of FIG. 22 and a photograph of the result of the surface treatment process.
Figure 22:
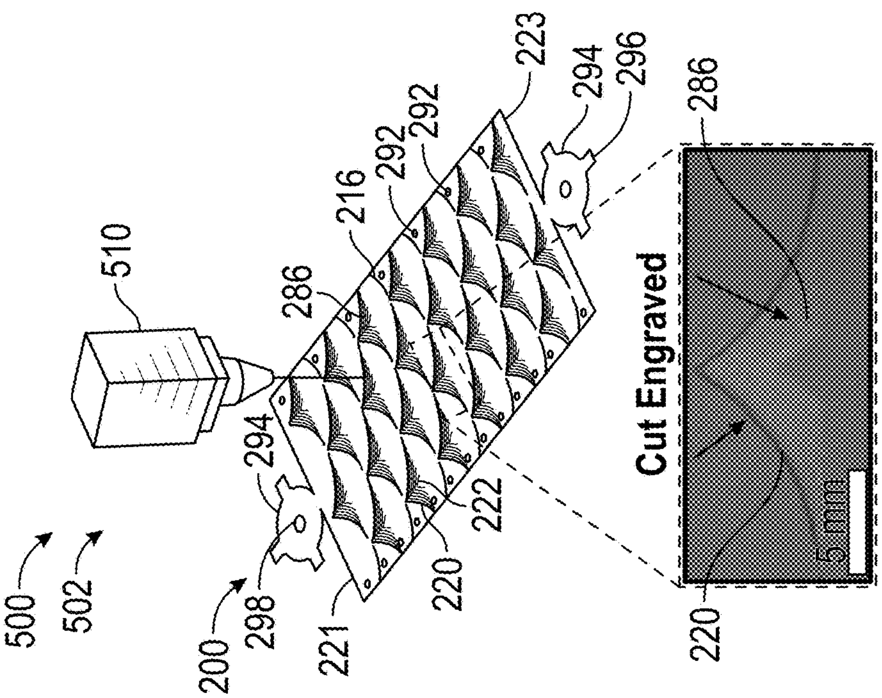
FIG. 22 illustrates a perspective view of a cutting process for making an outer shell of a kirigami-inspired spent and a photograph of the result of the cutting process.

Referring now to FIGS. 22-24, a non-limiting example of a method 500 of making the outer shell 216 for the stent 200 is illustrated. It is to be understood that the following method 500 can be applied to each of the stents described herein (e.g., stent 10, 100, 200). In the following description reference will be made to the stent 200 of FIGS. 13-14. As illustrated in FIG. 22, the stent 200 can be cut 502 from a flat sheet of material, and then later formed into a cylindrical shell 508. In the illustrated non-limiting example, the cuts 220 were formed via a laser cutter 510 (e.g., a $CO_2$ laser). In the specific illustrated non-limiting example, the stent 200 is composed of a periodic array of 2×13 projection elements 222 (e.g., 26 projection elements). Although, other configurations of arrays and total number of projection elements are also envisioned. As illustrated in FIG. 22, the laser cutter 510 can also form the etched striations 286 on the outer surface of the outer shell 216. For example, the laser cutter 510 can form the cuts 220 at a first power and the striations 286 can be formed at a second power that is lower than the first power.

According to some non-limiting examples, the outer shell 216 can include small apertures 292 perforated along lateral edges of the outer shell 216, which can be used to facilitate alignment when formed into a cylindrical shape. According to the illustrated non-limiting example, circular cutouts 294 can be coupled to the first and second ends 221, 223 of the outer shell 216. The circular cutouts 294 can be configured as end caps for the outer shell 216 when formed into a cylindrical shape. In the illustrated non-limiting example, the circular cutouts 294 can include one or more tabs 296 extending outward from the circular cutouts 294. The tabs 296 can be configured to be coupled to the first and second ends 221, 223 of the outer shell 216 (e.g., via an adhesive) to secure the circular cutouts 294 to the outer shell 216. The circular cutout 294 arranged at the first end 221 of the outer shell 216 can include a central aperture 298. The central aperture 298 can be configured to receive the inlet port 274 (see FIG. 13) such that the inlet port 274 can extend axially away from the outer shell 216 through the first end 221 thereof.

As illustrated in FIG. 23, some surfaces (e.g., such as plastic surfaces or surfaces comprised of elastomeric materials) can be hydrophobic, which can lead to incompatibility with surface coatings, such as therapeutic agent coatings. To increase the adhesion bond to surface coatings, an air plasma treatment 504, 506 can be utilized to micro clean and alter the surface properties of the kirigami surfaces for adhesion improvement. According to one non-limiting example, the surfaces of the outer shell 216 can be treated in air plasma 506 with high radio frequency for a predetermined period of time (e.g., at 500 mTorr for 1 hour) using a plasma cleaner device (e.g., a high power expanded cleaner). The plasma treatment results in the creation of hydrophilic surfaces of the outer shell 216 and improvement in the adhesive bond created between the outer shell 216 and surface coatings, such as therapeutic agent coatings like a drug-coated film, that can facilitate the drug solution coating and enhance the drug film stability.

According to some non-limiting example, a surface coating can include a radiopaque coating. For example, at least a portion of the outer shell 216 can be coated in a radiopaque coating. The radiopaque coating can make the outer shell 216 of the stent 200 radiopaque. According to some non-limiting examples, the entire outer shell 216 can be coated with the radiopaque coating. According to other non-limiting examples, at least the projection elements 222 can be coated with the radiopaque coating. According to some non-limiting examples, the outer shell 216 can be coated with a thin layer of tungsten filled conductive ink (e.g., RO-948 Radio Opaque Ink, MICROCHEM).

Finally, as illustrated in FIG. 24, the outer shell 216 can be formed into a cylindrical-shaped shell and the lateral edges can be coupled together (e.g., via an adhesive) with the outer surface with the striations 286 facing outward. In this configuration, the outer shell 216 can then receive an actuator (e.g., actuator 18, FIG. 5). Once the actuator 18 is within the outer shell 216, the circular cutouts 294 can be coupled to enclose the first and second ends 221, 223 (e.g., via an adhesive) (see, e.g., FIG. 13).

EXAMPLES

The following description includes particular non-limiting examples of stents that utilize the systems and methods previously described herein. The following examples are not intended to limit the disclosure. In the following description, a systematic study is described, in which the properties of the stents described herein are characterized using various parameters and tests.

Figure 25:
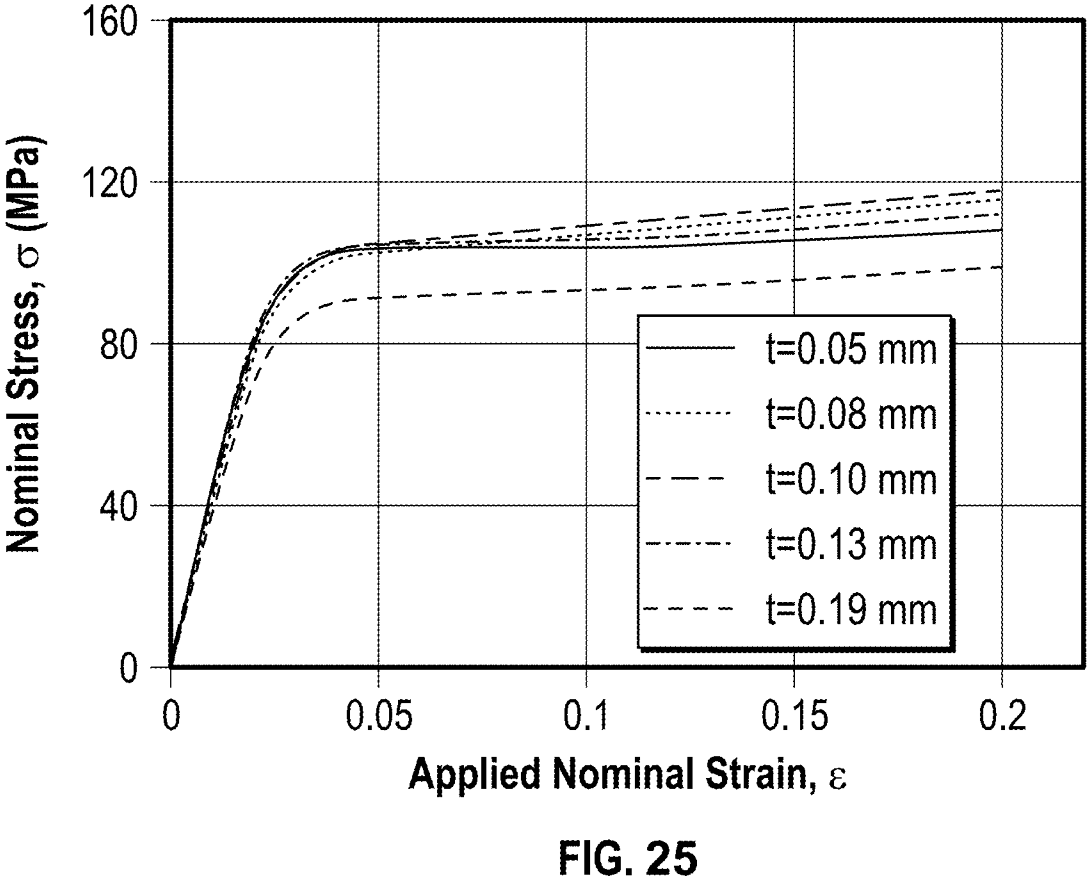
FIG. 25 illustrates nominal stress-strain curves for a tensile test characterizing a material for kirigami-inspired stents.

As described herein, the stents (e.g., stents 10, 100, 200) can include a cylindrical kirigami skin that includes a periodic array of snake denticle-like cuts, which can be embedded in thin plastic sheets. According to some non-limiting examples, color-coded polyester plastic shim stocks can be used to fabricate the kirigami surfaces with snake skin-like needles. To measure the material properties of the shim stocks, uniaxial tensile tests were carried out on the 80 mm×43 mm plastic specimens with a range of thicknesses, t=0.05, 0.08, 0.10, 0.13, 0.19 mm, according to ASTM D882-18 (Standard Test for Tensile Properties of Thin Plastic Sheeting). A uniaxial testing machine (e.g., an Instron 5942 series Universal Testing System) with a 500 N load cell was used to test specimens. All the tests were conducted under uniaxial tensile loading by applying a constant displacement rate of 0.5 mm/s quasi-statically until the 500 N load cell threshold. The response is characterized by linear elastic region followed by a plateau. Nominal stress-strain curves can be seen in FIG. 25. E=3.655 GPa and v=0.4 were the measured Young's modulus and Poisson's ratio of the plastic shim stocks, respectively.

Figure 26:
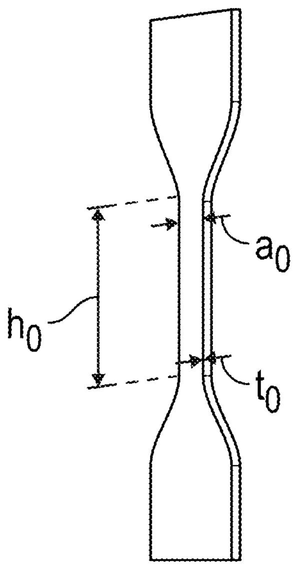
FIG. 26 illustrates a perspective view of an exemplary dogbone for a tensile test of a material for an actuator for a kirigami-inspired stents.
Figure 27:
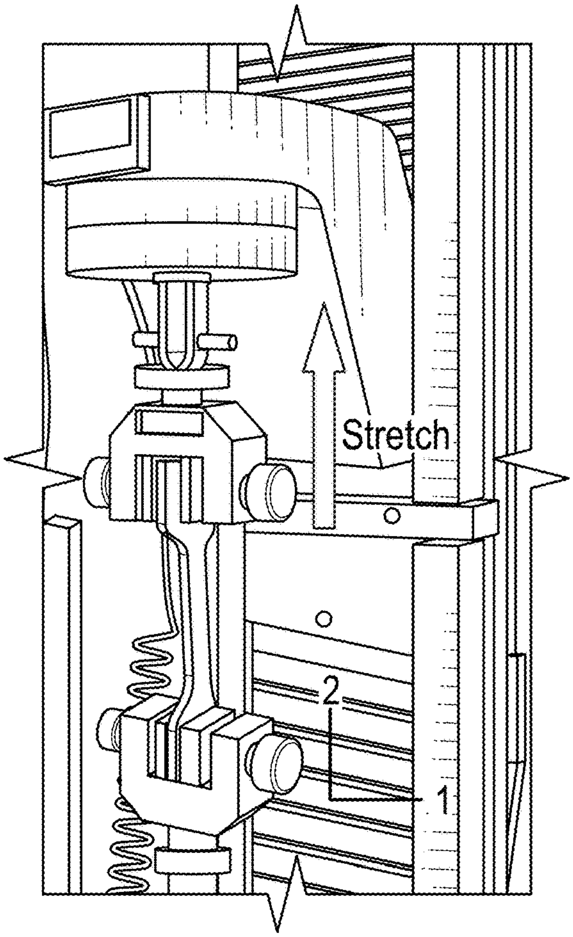
FIG. 27 illustrates an experimental setup for the tensile test for the actuator material.
Figure 28:
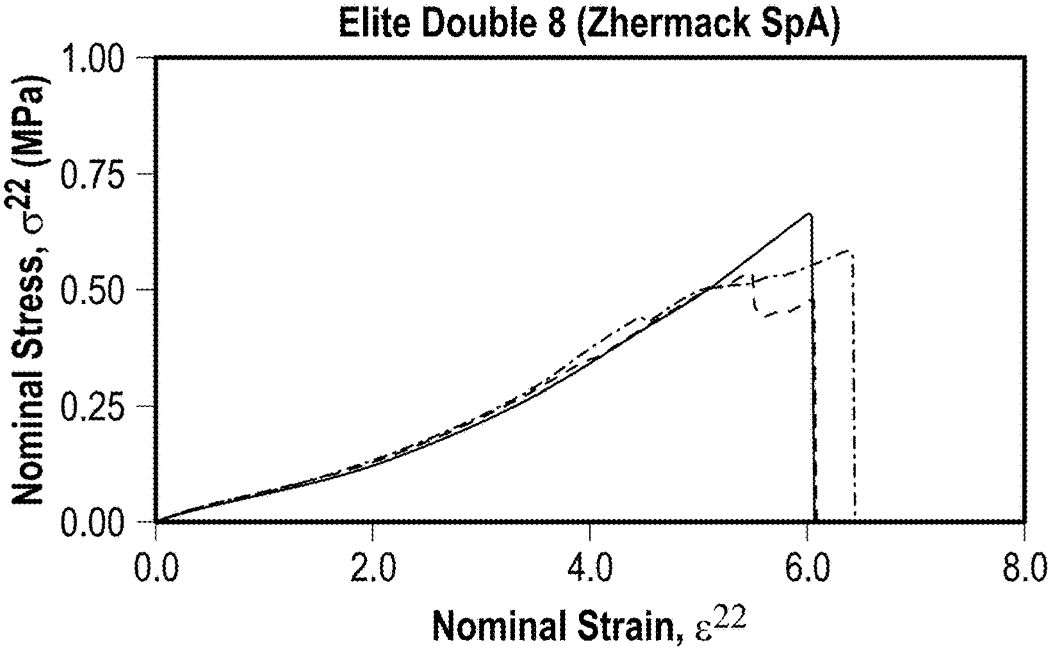
FIG. 28 illustrates nominal stress-strain curves for the tensile test characterizing the material for the actuator for the kirigami-inspired stents.

The stents can also include a pneumatic fiber-reinforced soft actuator made of a 1.5 mm thick silicone-based rubber. The silicone-based rubber can be Vinylpolysiloxane (a-silicone) duplicating elastomer (e.g., "Elite Double 8") was used to cast the soft actuator. To measure the material properties, three dog-bone specimens (FIG. 26, gauge length, $h_0$, of 33 mm, width, $a_0$, of 6 mm, and thickness, $t_0$, of 3 mm) were cast and tested under uniaxial tensile loading according to ASIM D412 Test Method (Standard Test Methods for Vulcanized Rubber and Thermoplastic Elastomers, Tension). A uniaxial testing machine (e.g., an Instron 5942 series Universal Testing System) with a 500 N load cell was used to test specimens. As illustrated in FIG. 27, one end of each specimen was fixed using screw side action grips, and a constant displacement rate of 500 mm/min applied to the other end quasi-statically. The stress-strain response of the material (i.e., nominal stress vs. nominal strain) was monitored up to the elastomer rupture at $\varepsilon \sim 6$ (FIG. 28). The nominal stress, $\sigma^{22}$, is defined as the force applied on the deformed sample, divided by the cross-sectional area of the undeformed sample. As illustrated in FIG. 28, the rubber has Poisson's ratio of $v_0$=0.499, density of ρ=1.0E3 kg/m3, and initial elastic modulus of $E_0$=79.267 KPa.

The pneumatic fiber-reinforced soft actuator can provide a linear motion to induce tensile strain in the kirigami skin and trigger the needles to pop out. The radial expansion ($\varepsilon^r$) and axial extension ($\varepsilon^a$) of the stent and popping angle of the needles (θ) can be tuned by controlling the actuator pressure ($P/P_0$), where $P_0$=1 atm.

Figure 29:
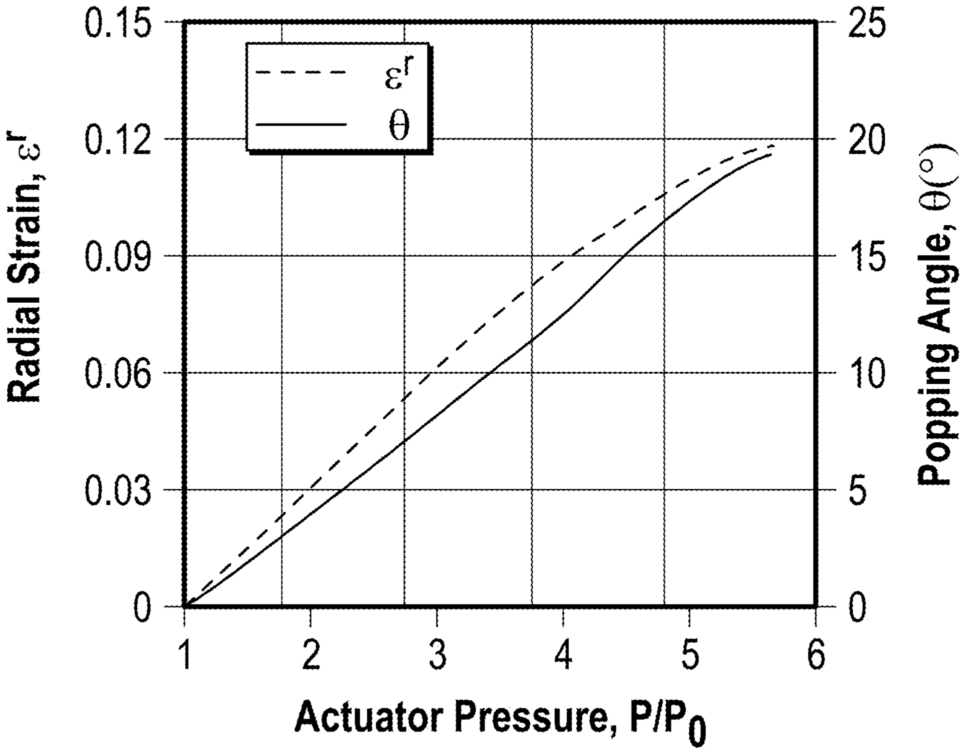
FIG. 29 illustrates the radial strain and needle angle as a function of actuator pressure for a kirigami-inspired stent.
Figure 30:
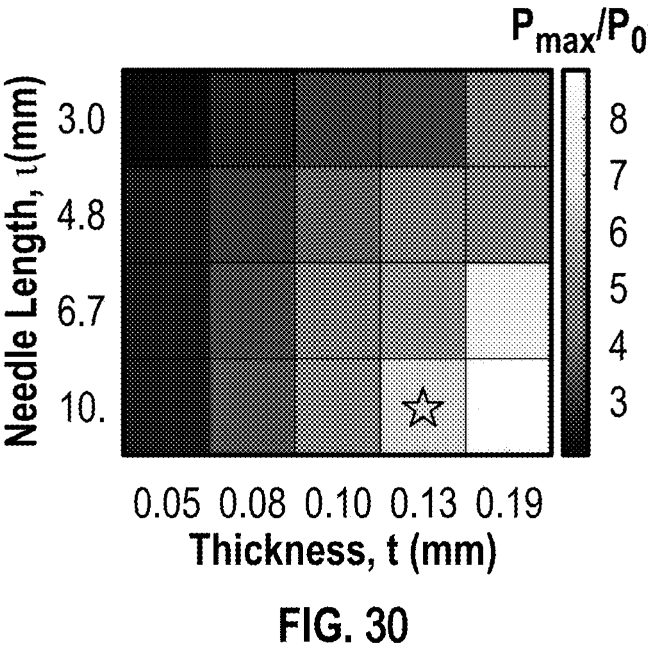
FIG. 30 illustrates a map of the effect of needle length and stent thickness on maximum actuator pressure.
Figure 31:
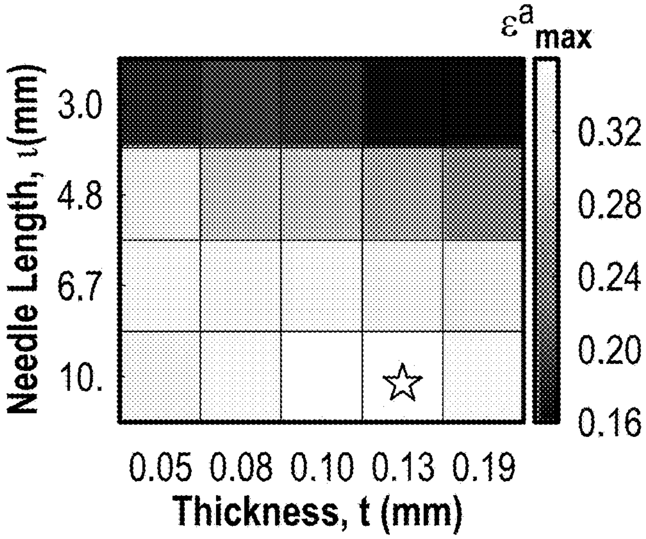
FIG. 31 illustrates a map of the effect of needle length and stent thickness on maximum axial strain.
Figure 32:
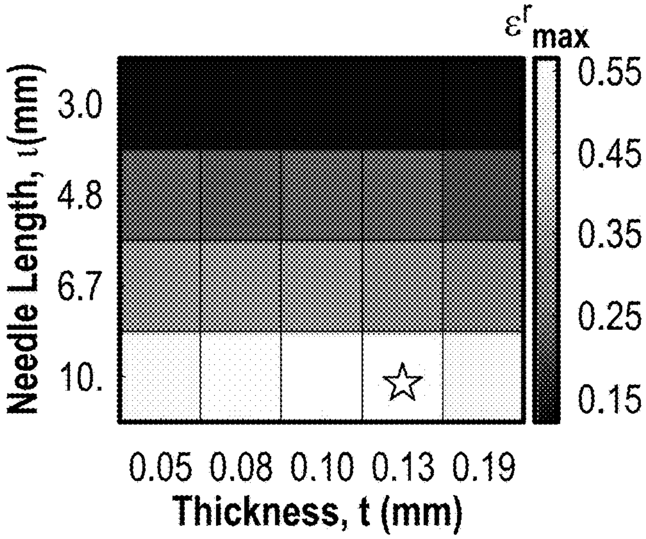
FIG. 32 illustrates a map of the effect of needle length and stent thickness on maximum radial strain.
Figure 33:
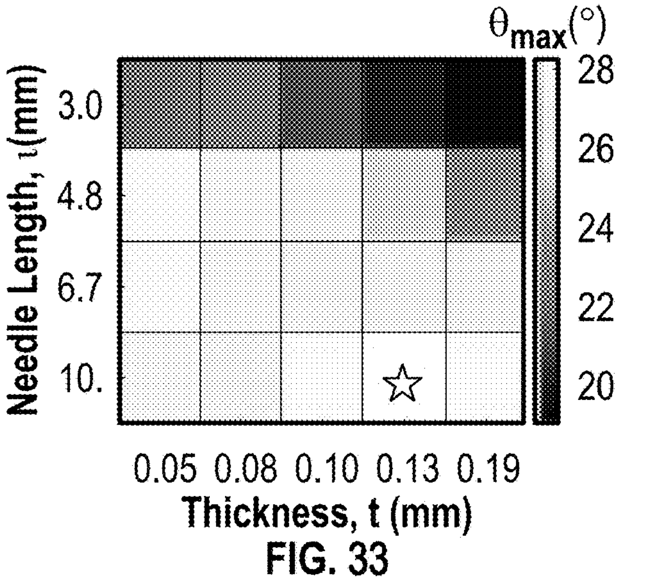
FIG. 33 illustrates a map of the effect of needle length and stent thickness on maximum needle angle.

For example, FIG. 29 illustrates the radial strain and needle angle as a function of actuator pressure. As illustrated, the needle angle the needle angle θ can be substantially proportional to the actuator pressure. In the illustrated non-limiting example, the needle angle θ can be linearly proportional to the actuator pressure. For example, as illustrated, $\varepsilon^r$ and θ are monotonically increased by 0.12 and 20° through applying pressure up to 5.8 atm for the with initial length $L_0$=8 cm and outer diameter $D_0$=12.5 mm.

Numerical models of the kirigami stents can be constructed with different combinations of t and l, and non-linear finite elements (FE) analyses can be employed to capture the deformation of the stents subjected to the applied actuator pressure using a FE package such as ABAQUS/Explicit. All the simulations were carried out using the commercial Finite Element (FE) package ABAQUS 2017. The Abaqus/Explicit solver was employed for the simulations. FE models were constructed of the elastomer actuator, Kevlar fiber, nylon plastic plug, and kirigami plastic shell to investigate the deformation response of the kirigami stent.

A linear elastic material model was used for Kevlar fiber, polyester plastic, and nylon plastic. Kevlar fiber has a density of 1.13E3 kg/m3, Young's modulus of 31067 MPa, and Poisson's ratio of 0.36 with a circular beam section of 0.0889 mm radius. Polyester plastic sheet has a density of 1.13E3 kg/m3, Young's modulus of 3655 MPa, Poisson's ratio of 0.4 with shell section of 0.127 mm thickness. The nylon Plastic has a density of 1.15E3 kg/m3, Young's modulus of 4000 MPa, and Poisson's ratio of 0.36. The constitutive behavior of the elastomer was captured using a nearly-incompressible Neo-Hookean hyperelastic model (Poisson's ratio of v_0=0.499 and density of 1.0E3 kg/m3) with directly imported uniaxial test data described in "Material characterization" for silicone-based rubber.

Different element types were used to construct the three-dimensional (3D) FE models of the kirigami stent. Linear beam element (Abaqus element type B31, seed size=1) for the Kevlar fibers, 3D shell element with reduced integration (Abaqus element type S4R, seed size=1) for the plastic kirigami, and 3D brick element (Abaqus element type C3D8, seed size=1.5) for the elastomer actuator and the plastic plug. The Dynamic Explicit solver with a time period of 1000 and a mass scaling factor of 1000 (to facilitate convergence) was used. TIE constraint (surface to surface) was applied between the fibers and the elastomeric body. General Contact type interaction with penalty friction coefficient 0.2 for tangential behavior and "hard" contact for normal behavior were applied. Finally, the pressure load applied to the inner surface of the linear actuator using SMOOTH step amplitude curve, and the deformation of the kirigami stent model was monitored as a function of the applied pressure.

Using the numerical methods, as will be described below, an optimal stent design was identified that exhibits larger radial expansion ($\varepsilon^r$) and higher out-of-plane stiffness of the needles ($K^{33}$) for better engagement with the surrounding tissue and injection while actuated.

A systematic study was carried out to predict the effect of t (the thickness of the outer shell of the stent) and l (the needle length) on the evolution of $\varepsilon^a$, $\varepsilon^r$, and θ as a function of the applied actuator pressure ($P/P_0$) for an esophageal-sized stent with $L_0$=8 cm and $D_0$=12.5 mm. The deformation response of the kirigami stents can be controlled by varying the thickness of the kirigami shell (t) and the needle length (l) as a function of applied pressure. For example, FIGS. 30-33 illustrate the effect of l and t on the maximum actuator pressure ($P_{max}/P_0$, $P_0$=1 atm), maximum axial ($\varepsilon_{max}{}^a$), radial ($\varepsilon_{max}{}^r$) strains, and maximum popping angle ($\theta_{max}$) of a kirigami inspired stent.

In the color maps shown in FIGS. 30-33, where the actuator pressure $P_{max}/P_0$ (FIG. 30) that achieves a corresponding $\varepsilon_{max}{}^a$ (FIG. 31), $\varepsilon_{max}{}^r$ (FIG. 32), and $\theta_{max}$ (FIG. 33) of the stent is reported. Geometrical parameters were explored, ranging from t=0.05, 0.08, 0.10, 0.13, 0.19 mm and l=10.0, 6.7, 4.8, and 3.0 mm. The figures indicate that by increasing l, $\varepsilon_{max}{}^r$ considerably rises, and $\varepsilon_{max}{}^a$, $\theta_{max}$, and $P_{max}/P_0$ slightly increase for a given t Therefore, l=10.0 mm was selected as a good candidate for needle length to achieve maximum radial expansion. Furthermore, by increasing t, $P_{max}/P_0$ increases at constant l, however, $\varepsilon_{max}{}^a$, $\varepsilon_{max}{}^r$, and $\theta_{max}$ are almost remained unaltered.

Figure 34:
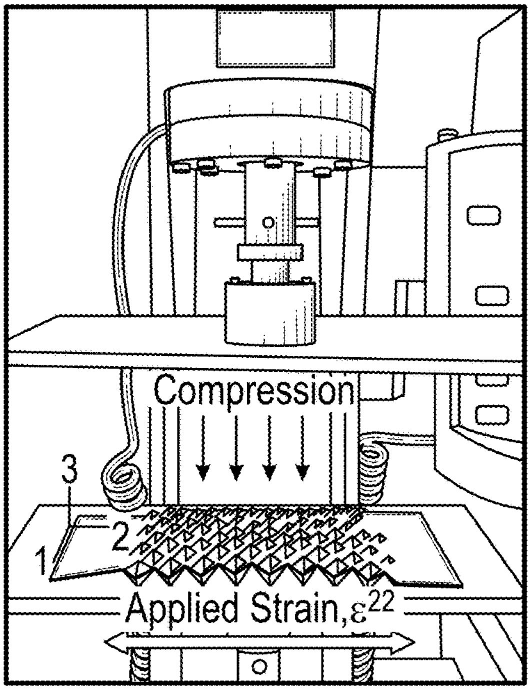
FIG. 34 illustrates an experimental setup for a stiffness test of needles of a kirigami-inspired stent in the normal direction.

To identify a preferred t for a given stent geometry, kirigami surfaces were fabricated with various thicknesses, and experimentally investigated the effect of t on the stiffness of the kirigami needles in the normal direction, denoted by $K^{33}$. To measure the stiffness, a normal stiffness test was carried out (e.g., using an Instron 5942 series Universal Testing System). First, the surfaces were uniaxially stretched to different levels of strains, ε^22=0, 0.5, 0.10, 0.15, and 0.20, which result in buckling out the needles. At each level of applied strain, the surfaces were immobilized to an acrylic plate and then compressed in the vertical direction, as illustrated in FIG. 34. Surfaces with barb-shaped needles made of plastic were tested. For each level of strain, the surfaces were compressed at a constant rate of 1 mm/s until flattened using a 500 N load cell. The compression force as a function of vertical displacement was recorded. The normal initial stiffness (N/mm) was then estimated by calculating the initial slope of the force-displacement curves. This was repeated three times per levels of applied tensile strain.

Figure 35:
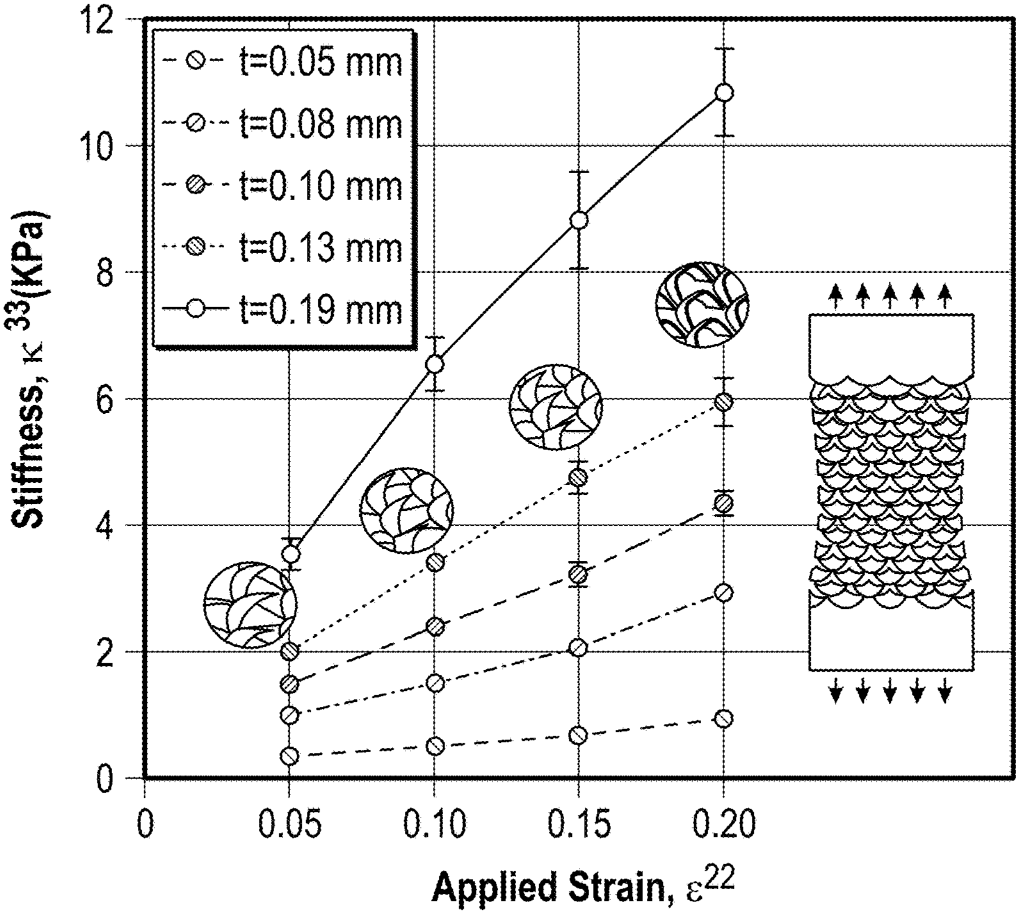
FIG. 35 illustrates the results of the stiffness test of FIG. 34.

FIG. 35 demonstrates that increasing t, significantly increases the out-of-plane stiffness of the needles. Therefore, choosing a thicker kirigami can result in stiffer needles that can provide easier penetrations. Since the kirigami with the maximum thickness (t=0.19 mm in grey) shows localized plastic zones at the hinges that slightly affects the reversible deformation of the needles (i.e., return to the initial flat configuration after releasing the load) needed for safe removal.

Figure 36:
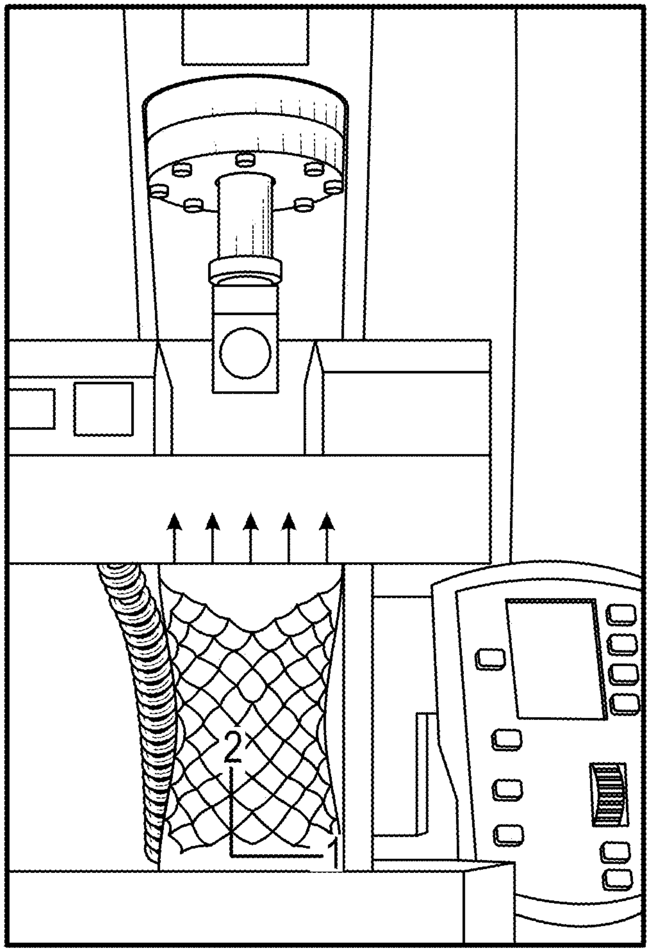
FIG. 36 illustrates an experimental setup for a uniaxial tensile test of a kirigami-inspired stent.
Figure 37:
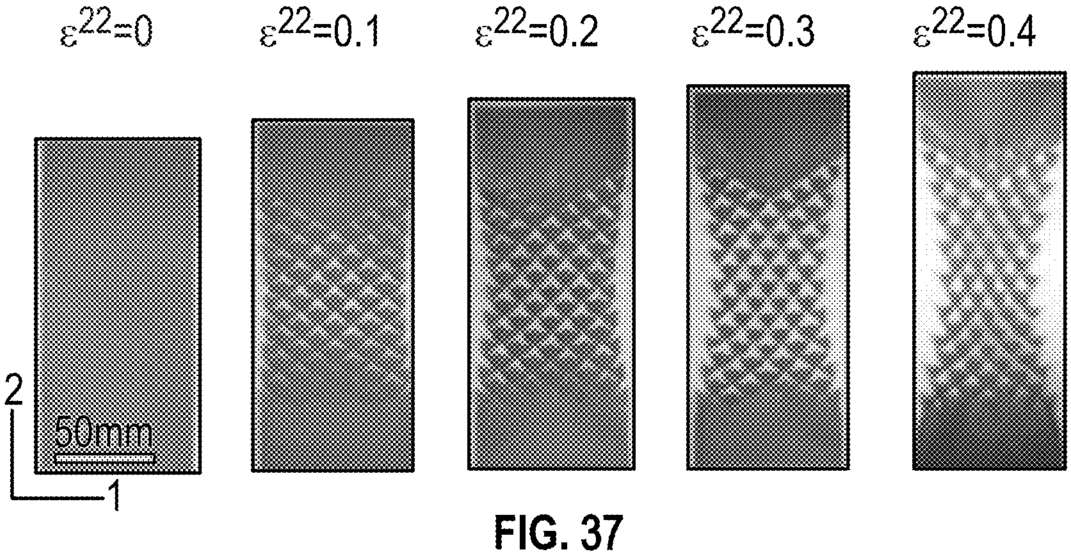
FIG. 37 illustrates experimental images showing undeformed and buckled configurations of a kirigami-inspired stent under different levels of applied strain.
Figure 38:
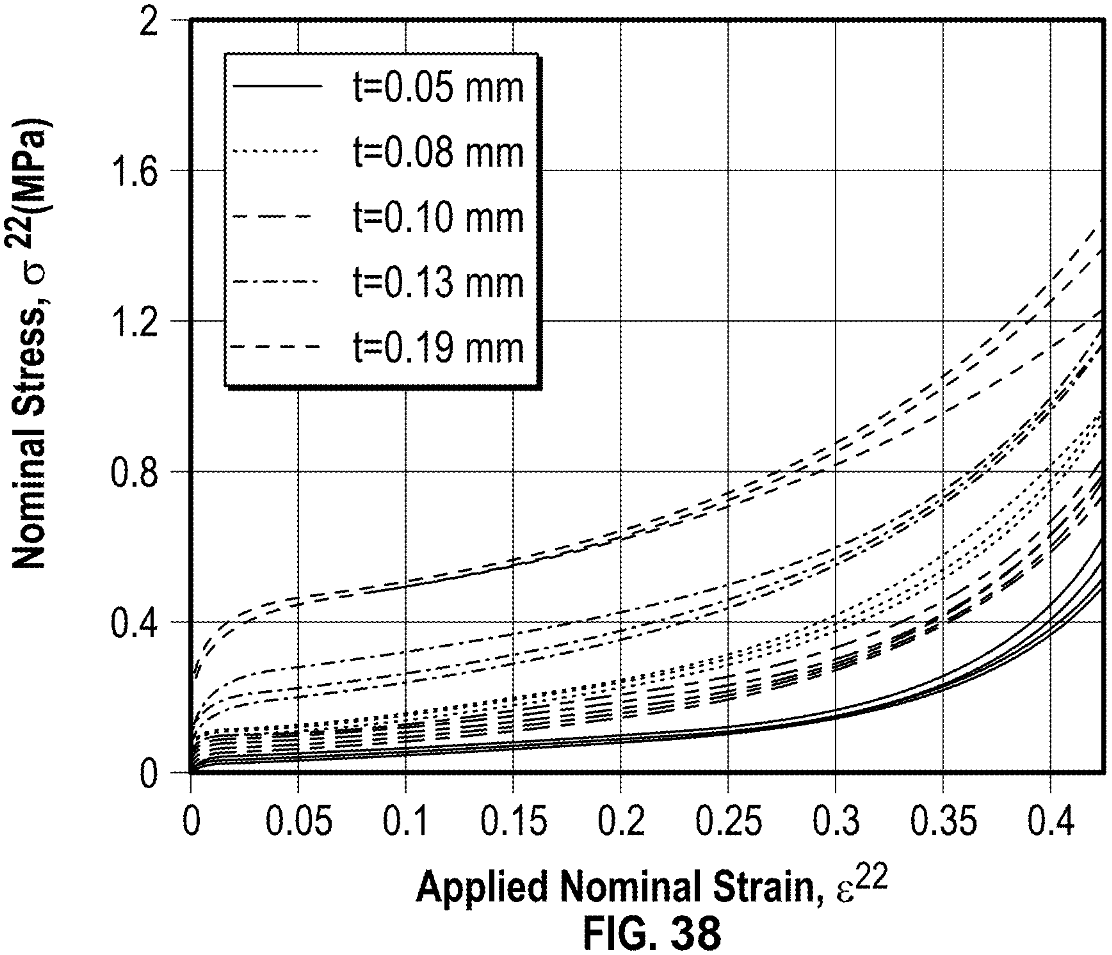
FIG. 38 illustrates nominal stress-strain curves of kirigami-inspired stents with various thicknesses.

As previously described, the kirigami shell (or stent) is capable of reversible shape transformation from flat configuration (for device delivery and removal) to 3D surfaces with popped-up needles (for injections) that enables facile delivery, robust deployment, and safe removal of the drug releasing system. FIG. 36 illustrates kirigami surfaces under uniaxial tensile loads. FIG. 37 illustrates experimental images showing undeformed and buckled configurations of the kirigami prototype under different levels of applied strain ε^22=0, 0.1, 0.2, 0.3, and 0.4. FIG. 38 Nominal stress-strain response of the kirigami surfaces with various thicknesses t=0.05, 0.08, 0.10, 0.13, 0.19 mm subjected to uniaxial tensile strain ε^22 for n=3 measurements. Given the systematic testing results, the kirigami with t=0.13 mm was selected as a preferred thickness for making the kirigami shell at the given stent geometry. Having identified l=10.0 mm and t=0.13 mm as ideal design parameters that provide simultaneous highest $\varepsilon^r$ and $K^{33}$, along with having reliable reversible shape transformation, the stent prototypes were fabricated, and their performance was experimentally evaluated.

Figure 39:
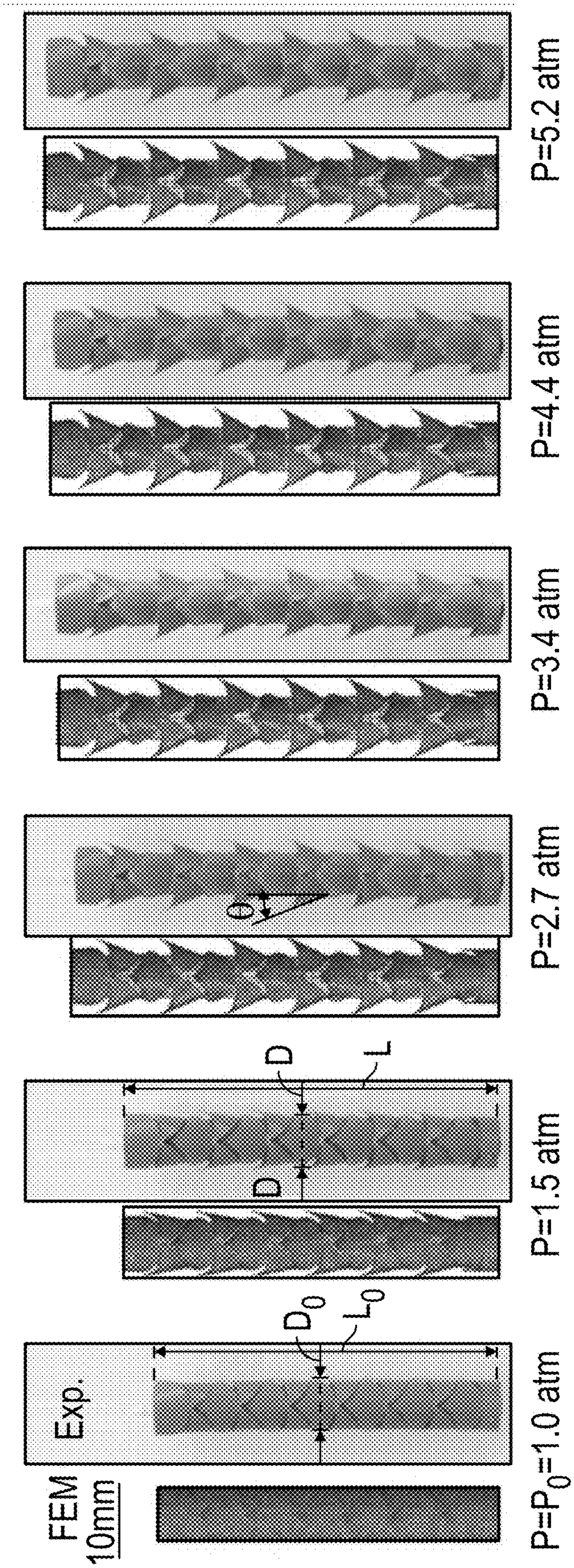
FIG. 39 illustrates numerical and experimental images of a kirigami-inspired stent at different levels of actuator pressure.
Figure 40:
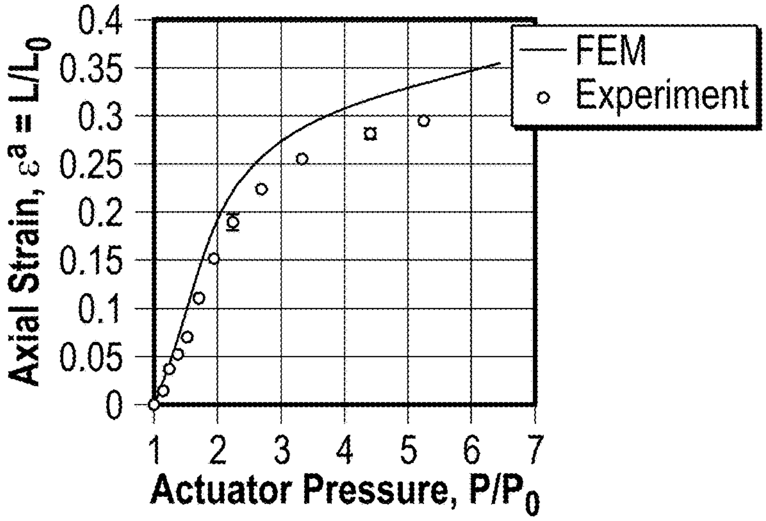
FIG. 40 illustrates numerical and experimental results of axial strain as a function of actuator pressure.
Figure 41:
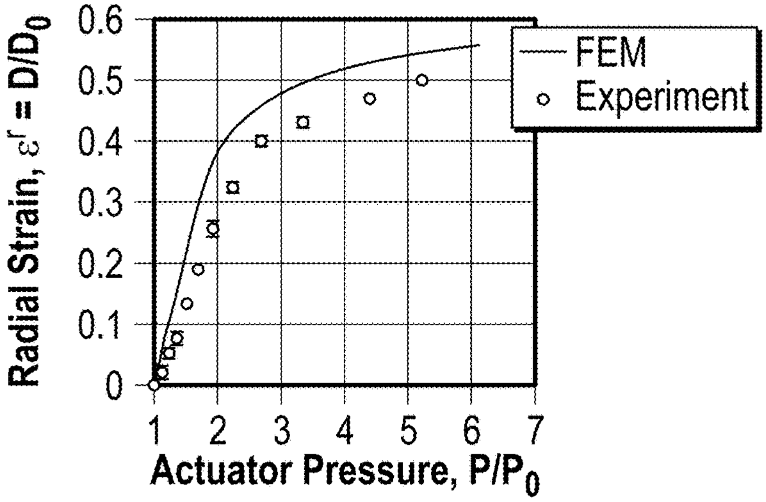
FIG. 41 illustrates numerical and experimental results of radial strain as a function of actuator pressure.
Figure 42:
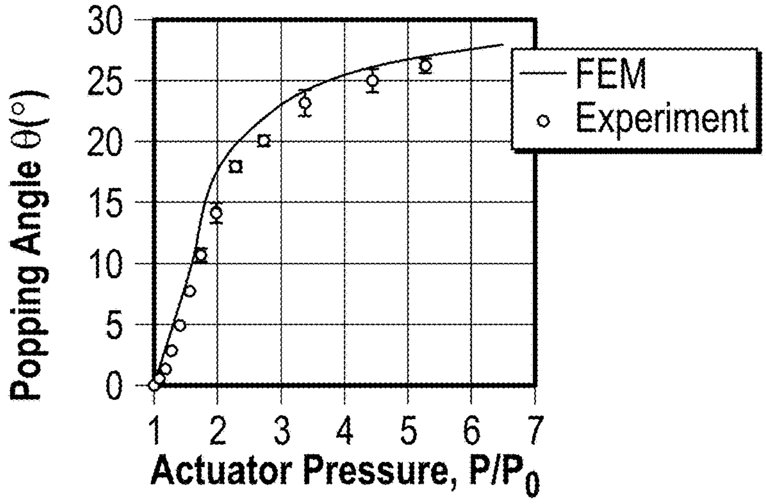
FIG. 42 illustrates numerical and experimental results of needle angle as a function of actuator pressure.

Referring now to FIG. 39, Numerical and experimental images of the esophageal stent at different levels of actuator pressure, P=1.0, 1.5, 2.7, 3.4, 4.4, and 5.2 atm, where P=1.0 and 5.2 atm correspond to undeformed and fully deployed configurations, respectively. $L_0$=8 cm and $D_0$=12.5 mm are the initial length and outer diameter, and L, D, and θ are the length, outer diameter, and popping angle of the stent for a given P, respectively. The kirigami stent in the illustrated images is formed from an 80×43 mm surface consisting of a periodic array of 2×13=26 stretchable needles. FIGS. 40-42 illustrate the evolution of axial strain ($\varepsilon^a$) (FIG. 40), radial strain ($\varepsilon^r$) (FIG. 41), and popping angle (θ) (FIG. 42) plotted as a function of $P/P_0$. Numerical calculations (red dashed line) are compared to experimental (blue markers) results. The markers represent the mean±SD for n=22 needle measurements for each group.

The experimental images were compared to the numerical snapshots obtained from non-linear FE simulations, showing that the kirigami shell is initially flat and then transform into 3D configurations with buckled out or protruding needles upon pressurizing the actuator. By releasing the pressure, the needles are popped in or retract and recovered their original undeformed shape. The deformation of the prototype was quantified and the experimental data (blue markers) was compared to the FE results (red dashed lines), showing a close agreement. The evolution of axial extension ($\varepsilon^a$=L/$L_0$), radial expansion ($\varepsilon^r$=D/$D_0$), and popping angle (θ) as a function of the actuator pressure ($P/P_0$) illustrated in FIGS. 40-42 demonstrate a gradual linear increase in $\varepsilon^a$, $\varepsilon^r$, and θ due to out-of-plane buckling of needles, and then a plateau at higher pressure up to $P/P_0$=6.5 results in $\varepsilon_{max}{}^a$=0.36, $\varepsilon_{max}{}^r$=0.57, and $\theta_{max}$=28°. This considerable expansion of the stent especially in the radial direction allows a close engagement of the popped-up needles against the tissue of a subject.

Figure 43:
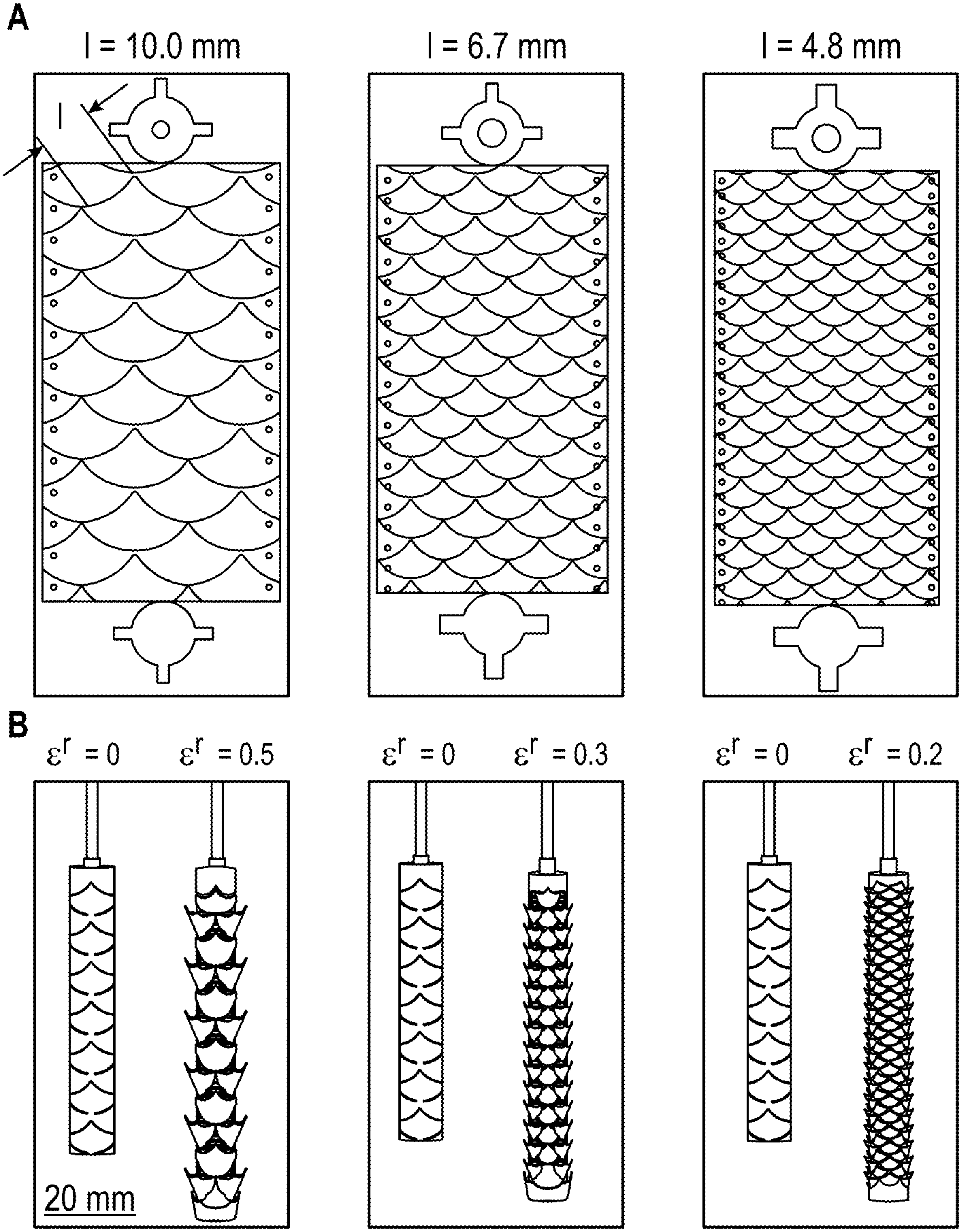
FIG. 43 illustrates kirigami-inspired stents with various needle lengths.

Finally, to ensure the ability to fabricate the stents in multiple sizes and consistency with this numerical prediction, further esophageal stents were fabricated with multiple combinations of t and l, and their deformation was characterized using both FE simulations and experiments, showing an excellent qualitative agreement. FIG. 43 (top) illustrates kirigami surface prototypes comprised of a period array of needles with various needle's lengths l=10.0 (left), 6.7 (middle), and 4.8 (right) mm made of t=0.13 mm kirigami surface. FIG. 43 (bottom) illustrates stent prototypes corresponding to the top kirigami surfaces at undeformed and actuated (at P/P_0=3.5 atm) configurations.

Evaluation of Controlled Penetration of Stent Needles to the GI Mucosa.

Figure 44:
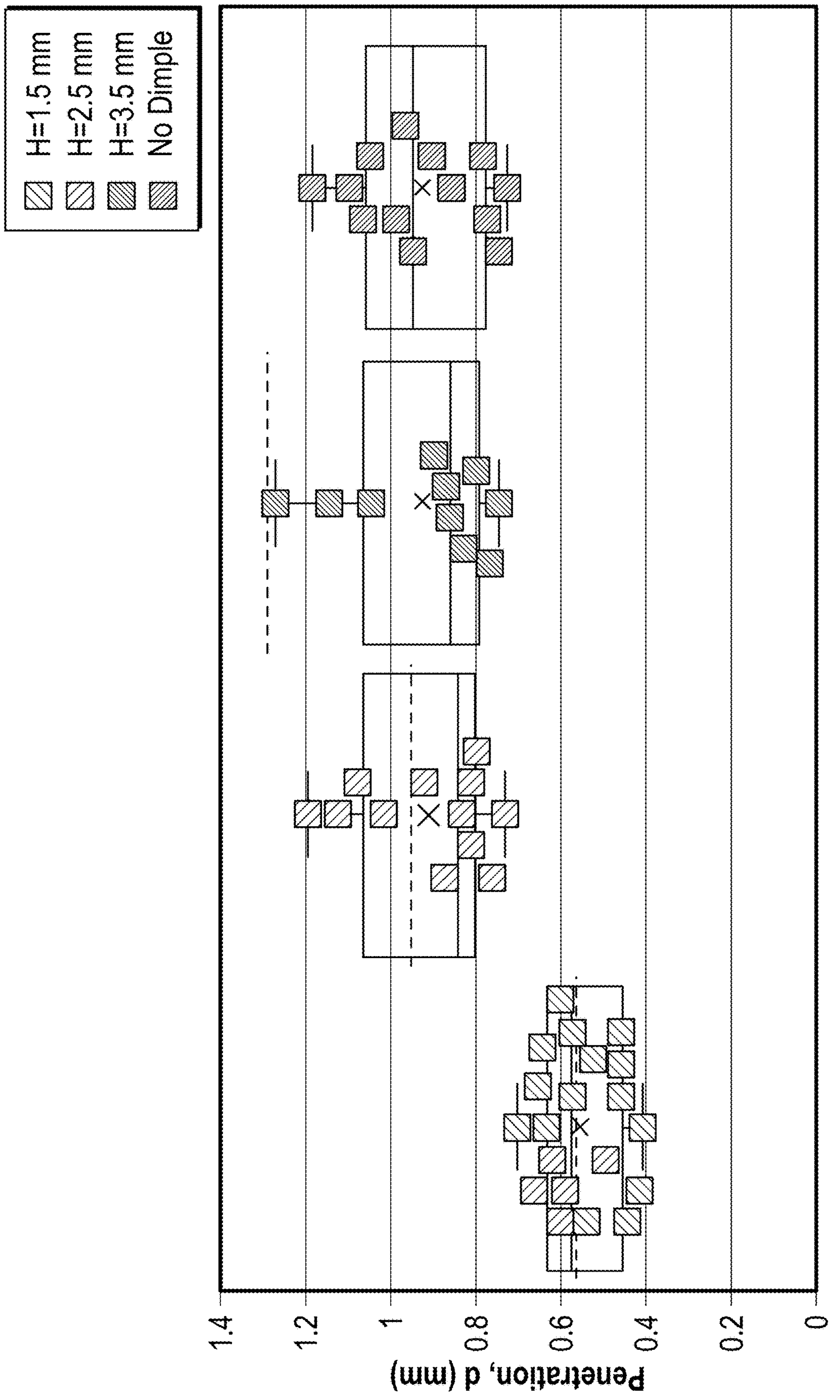
FIG. 44 illustrates experimental results of controlling needle penetration depth using protrusions along edges of a needle of a kirigami-inspired stent.

Micro-computed tomography (micro-CT) imaging and histology from ex vivo and in vivo experiments have been employed to demonstrate that the stent needles can be inserted by more than 1 mm into the submucosa of swine esophageal tissue without causing perforation. The penetration depth of the needles (d) can be controlled by incorporating the arc-shaped features (i.e., dimples with R=1.5 mm) on the two sides of the projection elements (i.e., needles) as illustrated in FIG. 44. These small features can stop further penetration when contacting the tissue surface. The dimples were positioned at a characteristic distance H from the tip of the needles. The experiments considered H=1.5, 2.5, 3.5 mm, and no dimple (control). To quantify d, stents were deployed in vitro and brushed with a thin layer of tungsten filled radio-opaque ink in the esophagi harvested from Yorkshire pigs using a custom 3D printed fixture.

To make the external surface of kirigami stent (especially the needles) radiopaque, the flat kirigami surfaces were coated with a thin layer of tungsten filled conductive ink (RO-948 Radio Opaque Ink, MICROCHEM) using a roller. The coated kirigami surface was left overnight to dry. The radiopaque stent prototypes with different needle's lengths (H) were deployed in the esophagus harvested from a Yorkshire pig. The esophagus was rinsed for approximately 10 sec under running tap water to wash away contaminants such as gastric fluid. To deploy the stent, a custom 3D printed fixture was used. The fixture consisted of a 20 mm diameter tube 3D printed out of VeroClear plastic. The 20 mm tube was placed inside the ex vivo esophagus to hold it open for deployment, and the stent with a given needle's length inserted into the esophagus via the tube. Once it reached the proximal esophagus, the pneumatic linear actuator inside the stent was inflated by pumping air using a plastic syringe connected to the stent (e.g., via the inlet port) via a Tygon PVC clear tubing results in popping up the needles. Syringe stopcock was used to maintain the pressure inside the stent's pneumatic actuator and keep all the needles popped up at the maximum angle (~22°) against the surrounding esophageal tissue. The kirigami needles were inserted into the tissue by gently pulling the Tygon tubing backward via application of ~8N force.

The deployed stent in the esophagus was then transferred into the micro-CT scanner and scanned following the protocol for soft tissue. Using the image viewer software, the penetration of the needles into the tissue was monitored by taking tomographic images at multiple views. The penetration depths were measured using both the cross-section and top views, where we were able to see the needle tips penetrated to the esophageal submucosa. The precise depths were obtained through measuring the distance between the inner surface of the tissue and the tip of the needles, d, as shown in FIG. 45.

Figure 45:
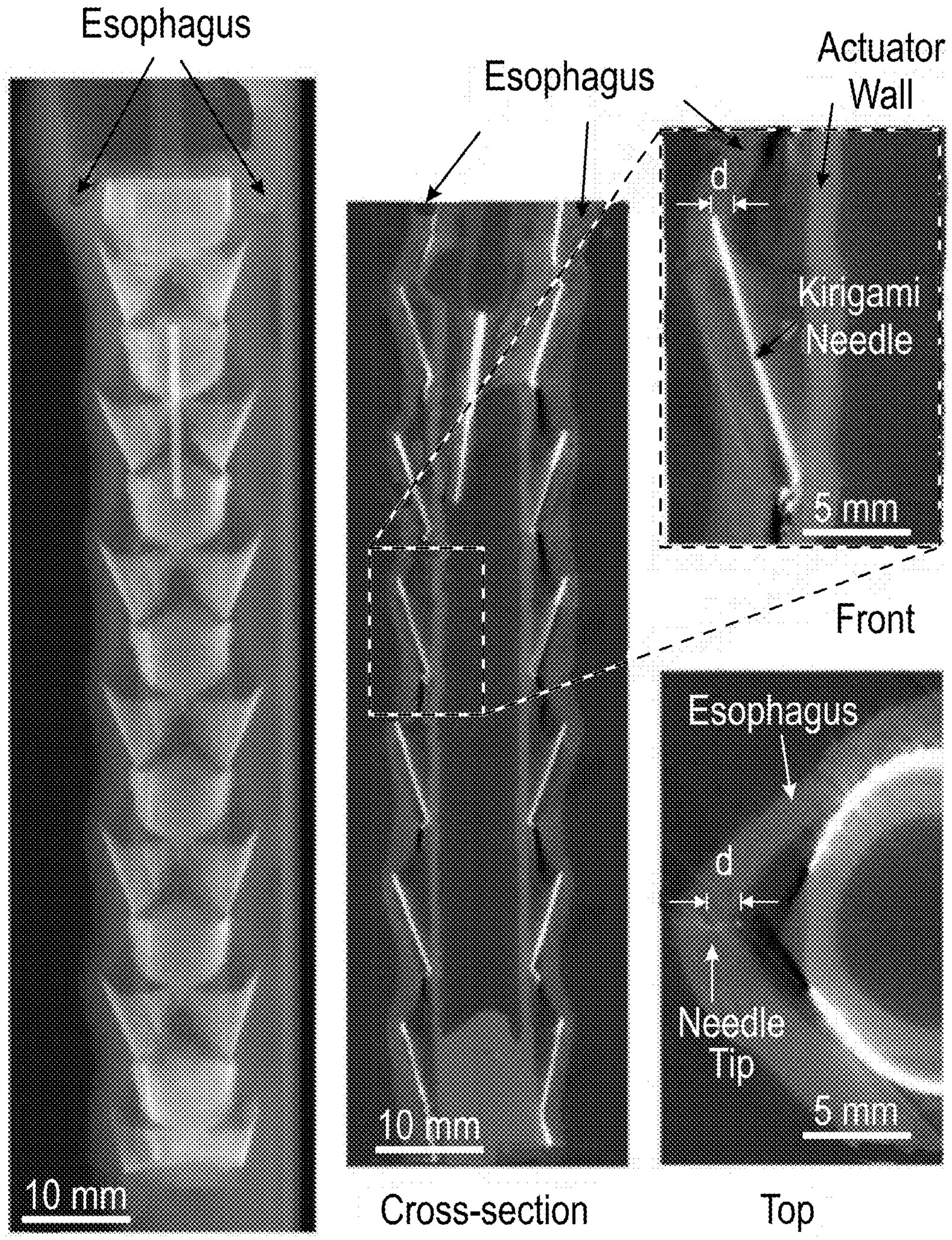
FIG. 45 illustrates a 3D micro-CT image of a deployed kirigami-inspired stent with 2D cross-sectional slices.
Figure 46:
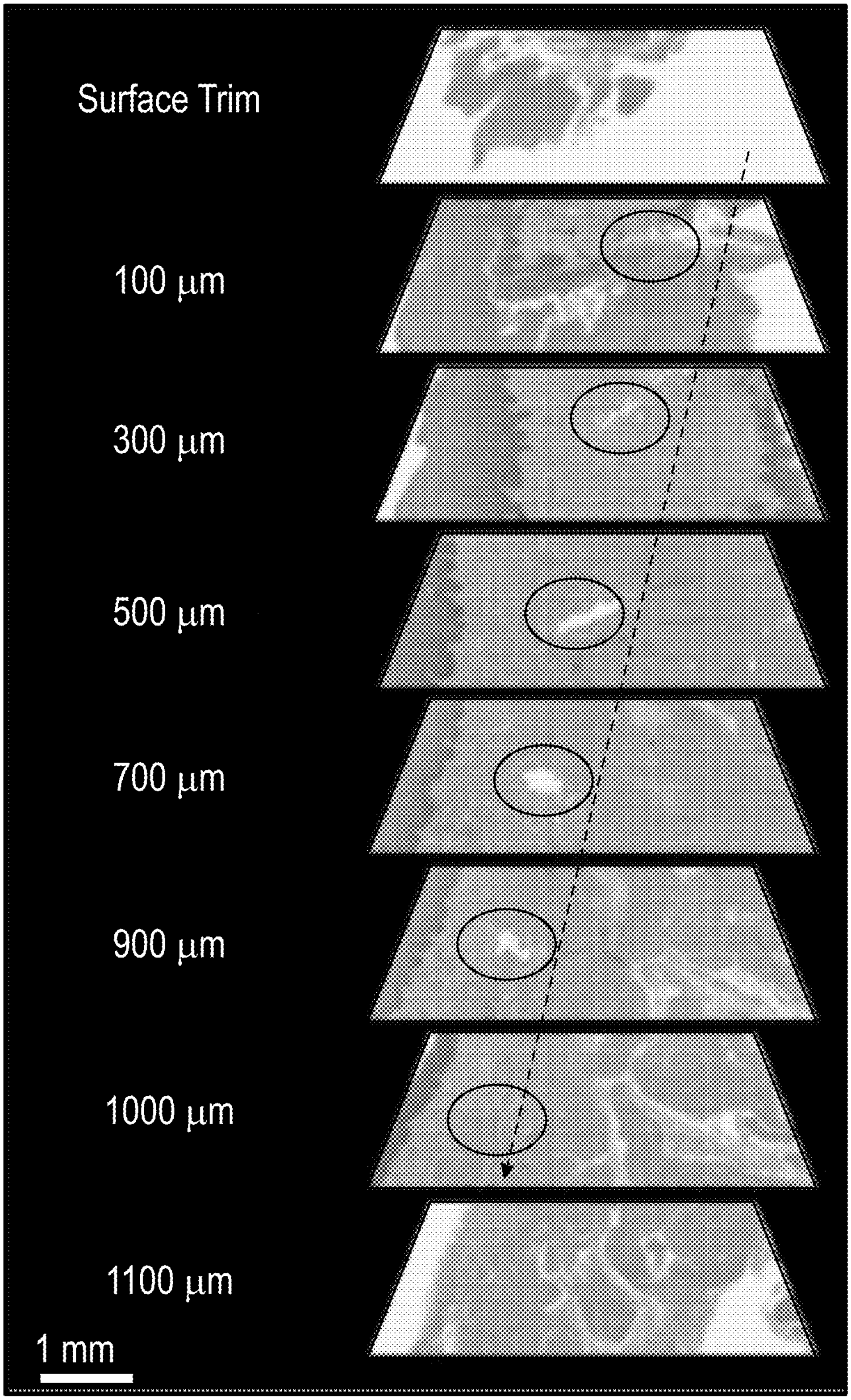
FIG. 46 illustrates histological image analysis performed in esophageal tissues at needle penetration sites.

FIG. 45 shows the representative 3D micro-CT image of the deployed stent and 2D cross-sectional slices used to obtain d. The data were reported in the plot (e.g., FIG. 44), showing d=0.549±0.092, 0.914±0.156, 0.926±0.176, and 0.932±0.148 mm for the stents made with H=1.5, 2.5, 3.5 mm, and no dimple, respectively (mean±SD, n≥10).

Note that all the needles were penetrated into tissues with an average tilting angle θ~22°, which is the maximum popping angle (considering the surrounding tissue wall) achieved by pressurizing the soft actuator up to $P_{max}/P_0$=6.5 and gently pulling it backward via application of ~8 N force. Therefore, the maximum penetration depths ($d_{max}$) were predicted as $d_{max}$=H sin θ=0.57, 0.96, and 1.34 mm for the needles 1 to 3 (dashed lines in FIG. 44 plot). For the needles with H=1.5 mm and 2.5 mm, the experimental results matched with the predicted $d_{max}$ verifying that the dimples were able to stop the insertion of the needles. However, the needle with H=3.5 mm did not reach $d_{max}$, demonstrating that for the given 8 N pulling force, the penetration depth of that needle is equivalent to the control needle that has no dimple. To ensure the safety margin on the insertion depth, the kirigami stent made of the control needle was deployed in vivo in pigs.

The kirigami stent prototypes were deployed for in vivo evaluations in a large animal model (50 to 80 kg female Yorkshire pigs ranging between 4-6 months of age). The pig was chosen as a model because its gastric anatomy is similar to that of humans and has been widely used in the evaluation of biomedical GI devices. An overtube (with D_in=⅝" and D_out=¾"—US Endoscopy), with endoscopic guidance, was placed into the proximal esophagus to assist the placement of the stent. The stent with 8 cm length and 12.5 mm diameter was inserted into the esophagus via the tube pushed by the end of a scope. Once it reached the proximal esophagus, the overtube was removed, results in exposure of the stent to the esophageal mucosa. Similar to the ex vivo deployment, the pneumatic linear actuator inside the stent was actuated by pumping air using a plastic syringe connected to the stent via a Tygon PVC clear tubing caused buckling up the needles. Syringe stopcock was used to maintain the pressure inside the pneumatic actuator and keep all the needles popped up against the mucosa. The kirigami needles were then inserted into the submucosa by gently pulling the Tygon tubing backward via application of ~8 N force. After deployment, the stent was left in place for 2 minutes before retrieval. The stent was then retracted by releasing the actuator pressure that makes the needles to buckle in and recover its original shape for easy removal.

Figure 48:
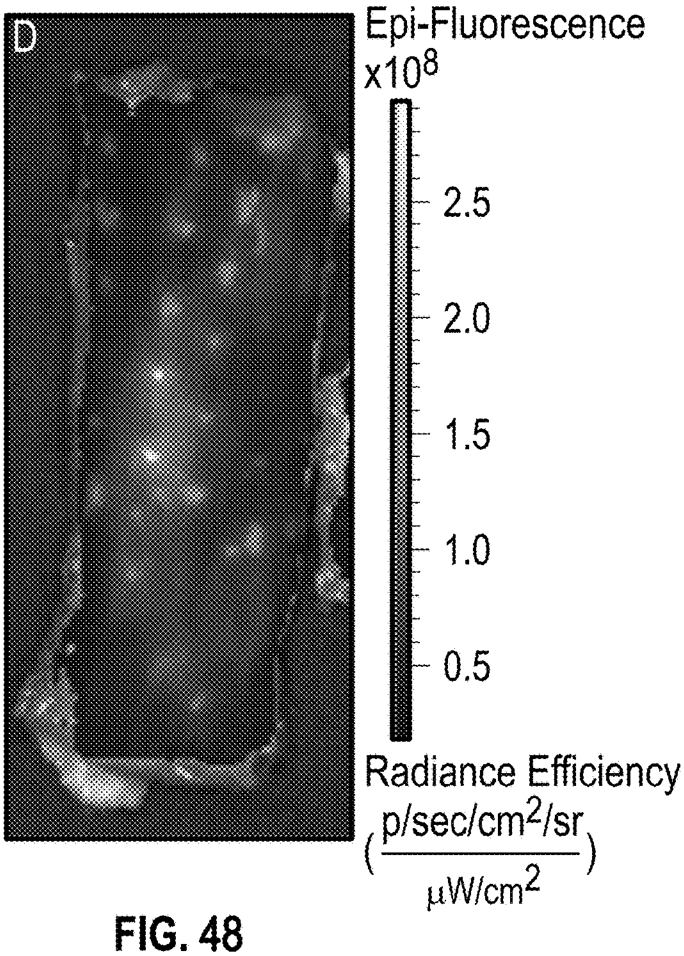
FIG. 48 illustrates a 2D epi-fluorescence image of needle penetration sites.

As illustrated in FIG. 48, a histological image analysis was performed of the esophageal tissues at the penetration sites, showing d=1.09±0.16 mm without perforation when 8 N force was applied. Biopsies were taken at the penetration sites of the harvested esophagi, where needles coated with tissue marking dye penetrated. The biopsies were fixed in formalin fixative for 24 hours before transfer to 70% ethanol. Tissue samples were then embedded in paraffin, cut into 5 μm-thick tissue sections, and imaged (e.g., by using an Aperio AT2 Slide Scanner).

In Vivo Delivery of Fluorescent Polystyrene Microparticle

To enable loading and delivery of polymeric particles with the injectable stent system, the external surface of the stent (i.e., kirigami shell) was coated with a solution of fluorescent magnetic polystyrene microparticles. Fluorescent magnetic polystyrene microparticles (Fluorescent Nile Red Magnetic Particles, 1.0% w/v, 4.0-4.9 μm nominal size) and 25% w/v of Dextran sulfate sodium salt in double-distilled H2O Water were mixed with a ratio of 5:2. 10% w/w of glycerol as a plasticizer was added to the mixture. The final mixture was vortexed for 10 minutes before coating.

Figure 47:
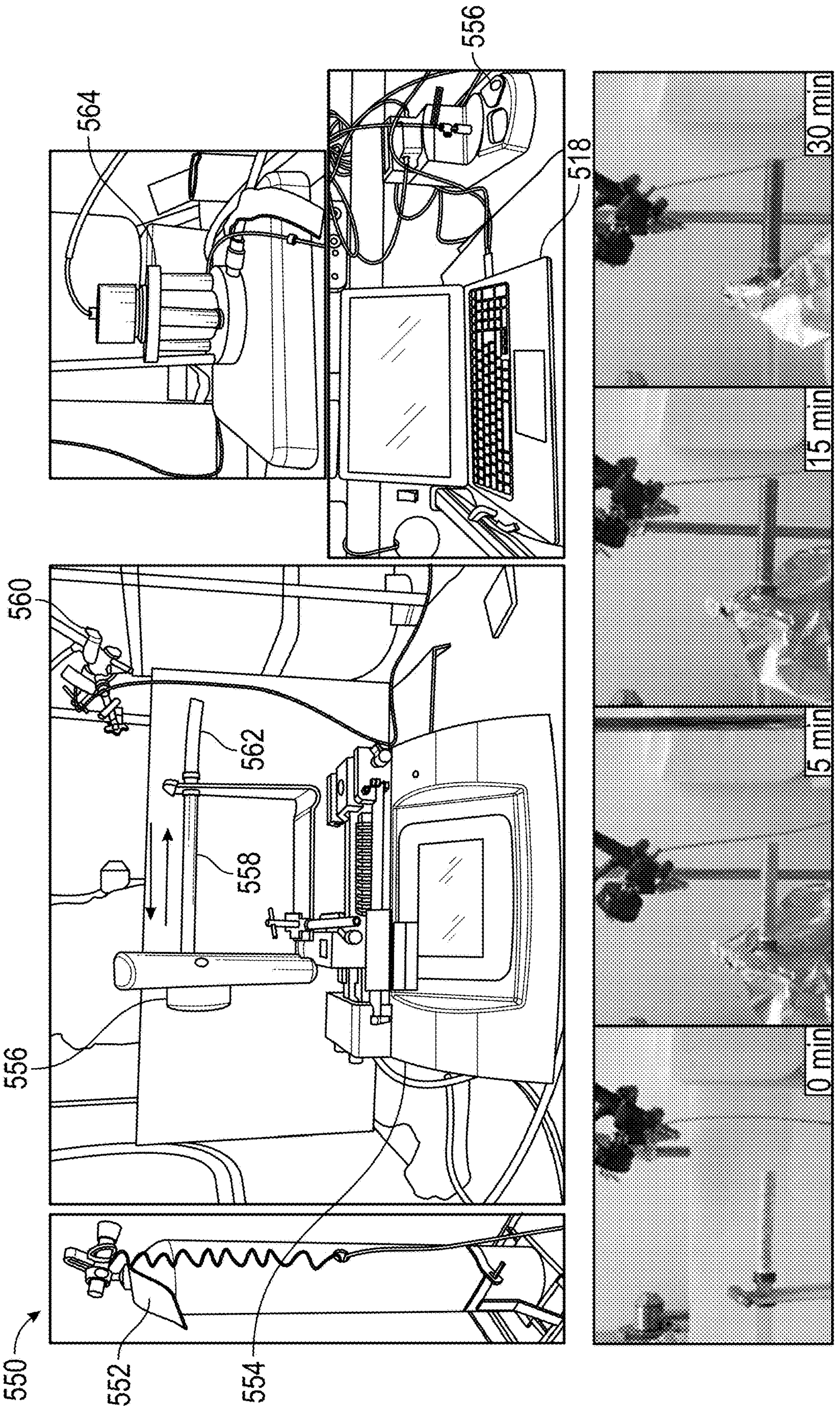
FIG. 47 illustrates images of an exemplary spray coating apparatus to apply coatings onto a kirigami-inspired stent.
Figure 49:
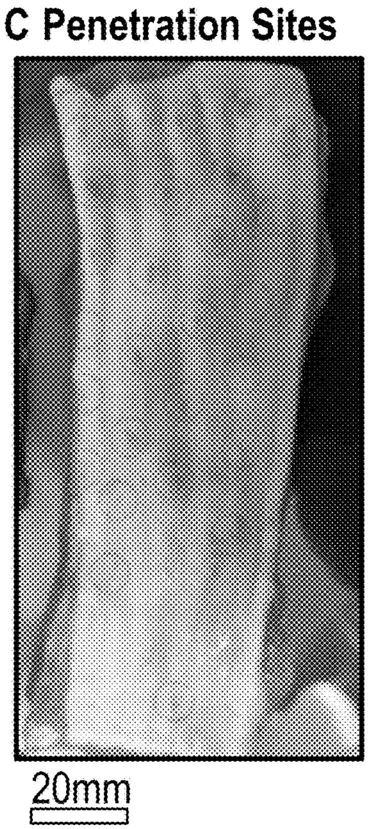
FIG. 49 illustrates an image of penetration sites.

A custom-built benchtop spray coating set-up with programmable stent movement and rotation was used to achieve a uniform thin film coating of the solution onto the kirigami stent shell, shown in FIG. 49. In the illustrated example, an airbrush controlled by a micro-fluidic pump and flow sensor was used to spray-coat the kirigami stent prototypes with fluorescent particle solution. The set-up 550 includes: nitrogen gas tank 552, standard infusion syringe pump 554, 20 rpm rotary fixture 556, 3D printed rotary shaft 558, airbrush 560, kirigami stent prototype 562 (e.g., stent 10, 100, 200), pressurized vessel containing the coating solution 564, micro-fluidic pump with a flow sensor 566, and PC controlling unit 568. The snapshots of the coating process at different time points (0, 5, 15, and 30 min) are illustrated in the bottom row of FIG. 47. One end of the shaft 558 was connected to a 20 rpm rotary fixture 556, while the other end held the stent prototype 562. The rotary fixture 556 was secured to a syringe pump 554 head, which provided a linear motion with 15 ml/min infuse or withdraw rate for a 50 ml target volume per coating step. This resulted in forward and backward motion (corresponding to infuse and withdraw steps) of the stent 562 with 24 mm/min speed for 8 cm displacement under a fixed airbrush 560, while the stent 562 rotates during the whole coating process. Such a rotation and linear motion ensure that the whole stent is covered with a uniform coating layer.

The airbrush 560—used to spray the coating solution through its nozzle—was connected with a silicone tubing to a 30 ml pressurized coating solution vessel 564 and placed on a magnetic stirrer for continuous mixing, feeding and spraying the solution. The vessel 564 was equipped with a pressure pump 566 controlled by software (e.g., on the PC controlling unit 568). Two nitrogen gas tanks 552 were used to supply pressure for the pressure pump 566 (400 KPa) and airbrush 560 (50 KPa) during the coating process. The feeding pressure was optimized (5-60 KPa) and set to 40 KPa (equal to 40 μl/min) to reach a constant solution flow and uniform spraying pattern. The whole coating process consisted of eight coating steps (four infuse and four withdraw).

The fluorescent magnetic microparticles were delivered in vivo in three porcine esophagi using the coated prototypes (FIGS. 48 and 49), which demonstrate a periodic array of higher fluorescent concentration spots at the kirigami needle penetration sites, further supporting the capability of this drug delivery system to administer polymeric particles to the GI tract. As illustrated in FIG. 48, the fluorescent red magnetic particles deposition in the harvested esophagus was assessed by taking a 2D epi-fluorescence image using an IVIS (in vivo imaging system) Spectrum in vivo imaging system at fluorescent excitation and emission filter set of 570 nm and 620 nm, respectively.

Figure 50:
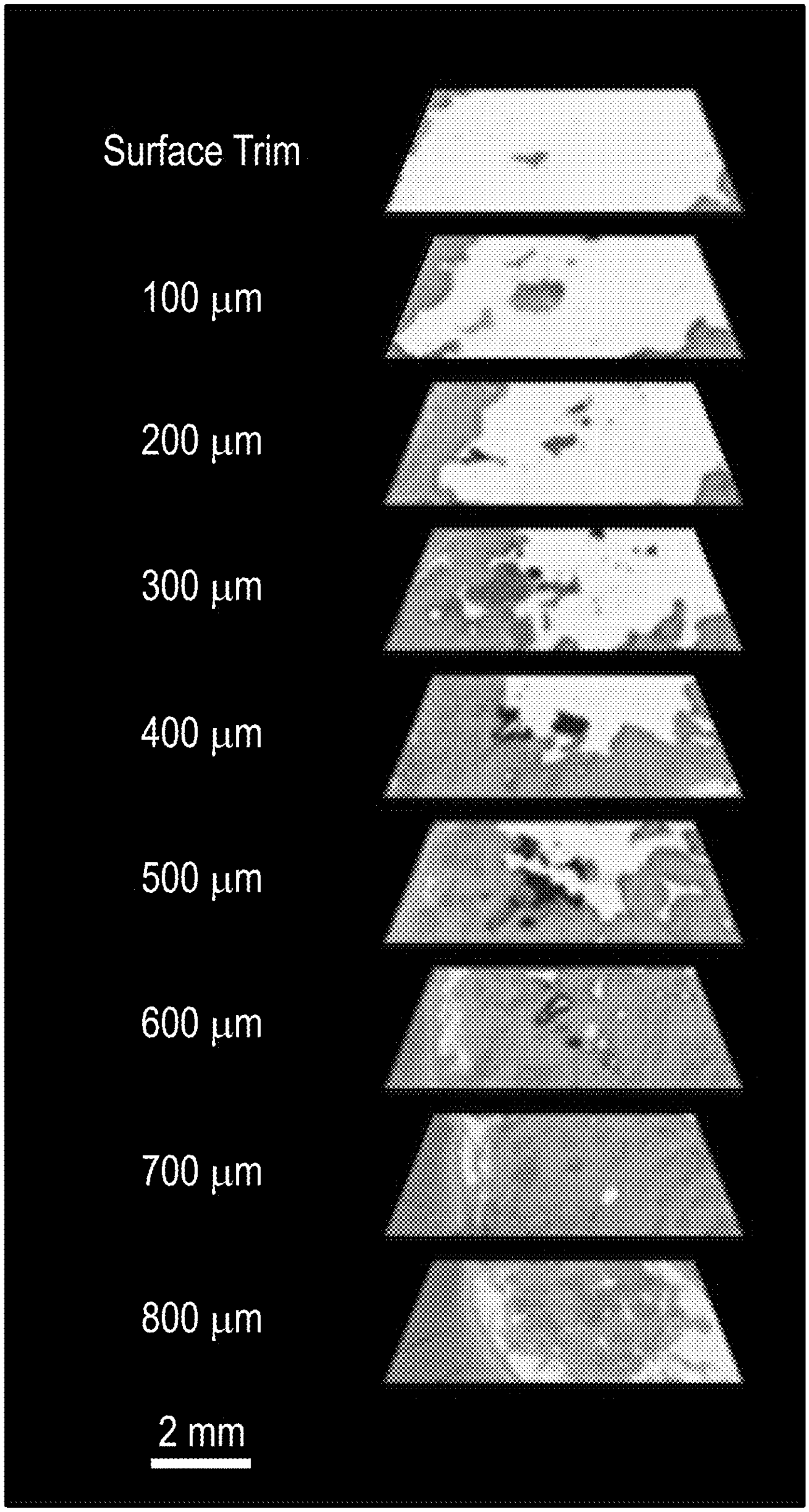
FIG. 50 illustrates histological image analysis performed in tissues of a trachea at needle penetration sites.

Similar kirigami-based stents with proper size and needle stiffness were prototyped to demonstrate the ability of safe delivery and circumferential injection of fluorescent microparticles in other tubular parts of the body including femoral arteries and trachea. For example, as illustrated in FIG. 50, histological images are illustrated of a trachea that was penetrated with kirigami-based stent needles having a tissue marking die thereon.

In vivo sustained drug release through deposition of polymeric particles loaded with therapeutics To evaluate the performance of the kirigami stents for extended drug release, in vivo studies were conducted in swine, and using budesonide as a model drug, demonstrating that the injectable stent delivers drug depots for up to a week through multipoint submucosal deposition of drug-loaded polymeric particles. Budesonide, an anti-inflammatory drug commonly used to treat inflammatory bowel disease and eosinophilic GI disorders, was encapsulated into poly lactic-co-glycolic acid (PLGA) microparticles using continuous microfluidic droplet generation method. Three formulations of budesonide loaded PLGA particles with 75, 100, and 125 mg/ml concentration of budesonide, were formulated and are denoted by BUD 75, BUD 100, and BUD 125, respectively. Additionally, 100 mg/ml concentration of fluorescent budesonide-PLGA particles (BUD 100F) was synthesized via the addition of a fluorescent agent.

Figure 51:
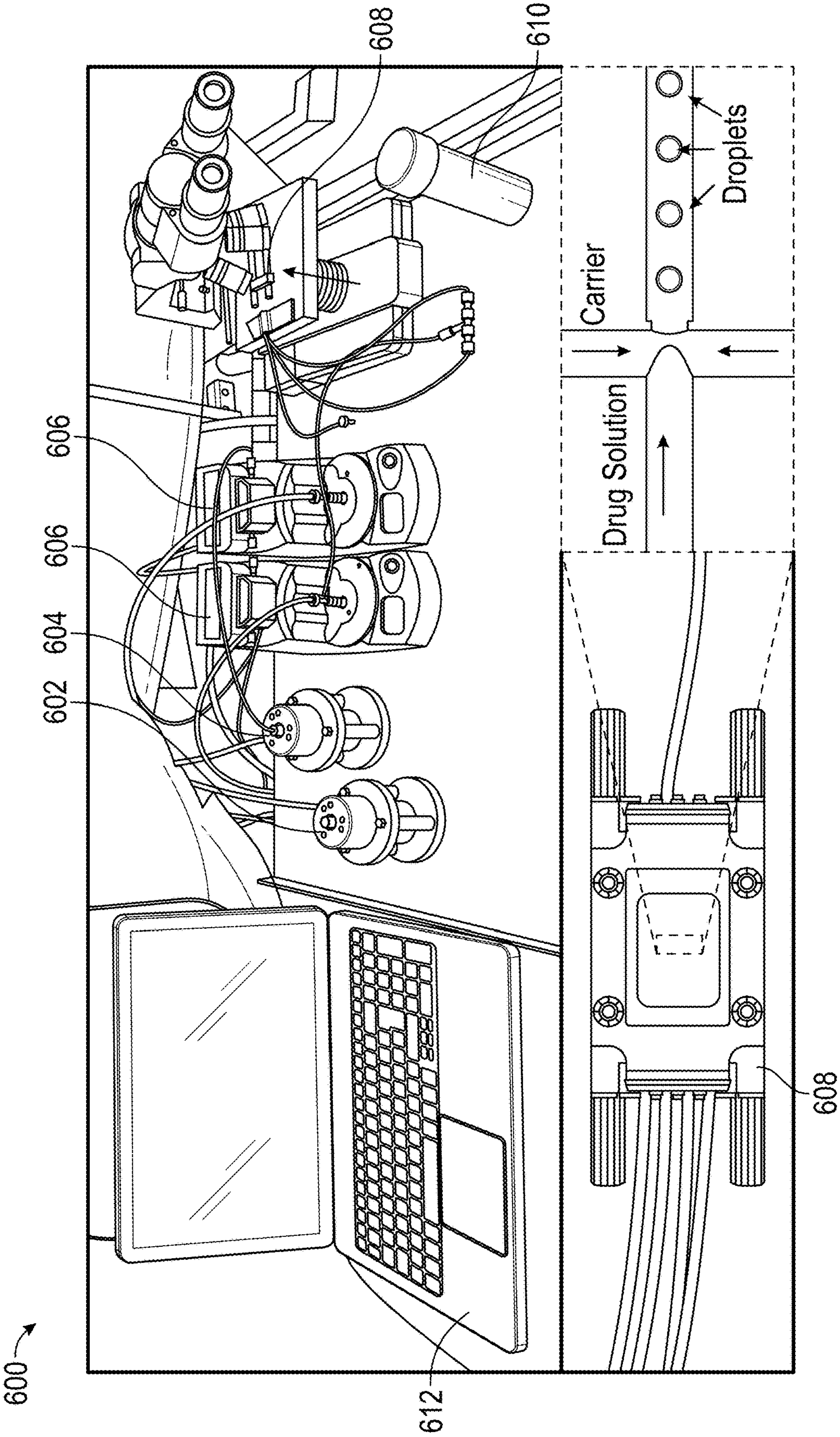
FIG. 51 illustrates images of an exemplary method of continuous microfluidic drug-PLGA droplet generation.

Budesonide-PLGA [Poly(D,L-lactide-co-glycolide) ester terminated, lactide:glycolide 75:25, Mw 76,000-115,000, Sigma Aldrich] microparticles were synthesized using a continuous microfluidic drug-PLGA droplet generation method, shown in FIG. 51. The set-up 600 includes: pressurized vessel 602 containing the Water/PVA mixture as aqueous stream, 30 ml pressurized vessel 604 containing budesonide and PLGA dissolved in DCM, pressure pumps 606 equipped with flow rate sensors for transferring aqueous and organic phases to the chip 608, one reagent 100 μm hydrophilic glass 3D flow-focusing microfluidic glass chip 608 and customized holder—see the magnified view of the channel configuration in the chip 608 in the bottom-left of FIG. 51, Siliconized glass stirred vessel 610 for collecting synthesized microparticles and solvent evaporation, and PC with software 612 for controlling pumps 606 with digital microscope interface for viewing and monitoring the droplet formation process.

The one reagent glass 3D flow-focusing microfluidic chip 608 with hydrophilic surface and 100 μm deep channels was used, followed by a solvent extraction step. Two partially miscible solvents including dichloromethane and water were used as drug solvent/carrier and droplets carrier phases, respectively. Budesonide (75, 100, and 125 mg/ml) and 1% w/v PLGA were dissolved in DCM as an organic fluid. 2% w/v PVA in double-distilled water was used as an aqueous/carrier phase for droplet generation. All fluids passed through a 0.2 μm pore microfilter before droplet production. To generate fluorescence-sensitive budesonide-PLGA particles, 0.3% w/v of PLGA-SH (LG 50:50, PolySciTech) and 20 μl of Alexa Flour 647 C2 Maleimide dye (Invitrogen) was also added to the budesonide-PLGA solution.

The microfluidic system set-up 600 includes two pressure pumps 606 equipped with in-line flow rate sensors to monitor and control the streams flow rates. Two flow rate sensors, 30-1000 μl/min and 1-50 μl/min, were employed in the organic line and aqueous line, respectively. An air compressor (not shown) provided the supply pressure for the pressure pumps 606 at 400 KPa working pressure. The pumps 606 were connected to 30/400 ml and 30 ml volume remote pressure chambers 602, 604 placed on magnetic stirrer for continuous mixing and delivering of PVA in water and DCM-PLGA-Budesonide solution to the chip 608 with 10 μl/min aqueous/carrier rate and 1.35 μl/min organic/drug-PLGA solutions rate, respectively. The particle synthesis process was continuously continued to reach 500 mg of particles while the DCM solvent was evaporating/by connecting the particle's collection siliconized stirred vessel to very mild vacuum pressure (about 650 Torr). Three formulations of budesonide-PLGA particles was synthesized with 75, 100, and 125 mg/ml concentration of budesonide, denoted by BUD75, BUD100, and BUD125, respectively. Additionally, 100 mg/ml concentration of fluorescent budesonide-PLGA particles (BUD 100F) was synthesized via addition of Alexa Flour 647 C2 Maleimide as described.

Figure 52:
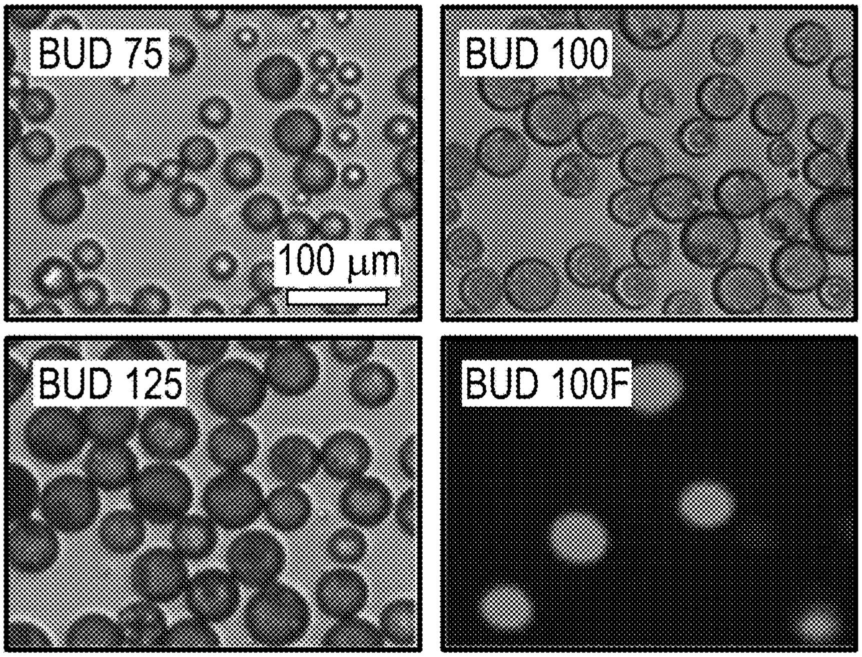
FIG. 52 illustrates morphological characteristics of synthesized drug particles.

FIG. 52 shows the morphological characteristics of the synthesized drug particles for the different formulations exhibit budesonide encapsulated into PLGA microspheres with experimentally measured size (diameter) distribution of 35.1±5.2, 43.0±5.6, 56.9±5.5, and 42.8±3.9 μm, encapsulation efficiency of 65.3±2.1, 59.3±1.5, 45.3±1.5, and 61.3±1.5 percent, and drug loading of 57.3±2.1, 54.5±1.5, 42.6±1.5, and 54.8±1.5 percent for BUD 75, BUD 100, BUD 125, and BUD 100F, respectively (mean±SD, n=80-100 particles for each formulation).

The size of the prepared formulations for the drug-loaded particles (BUD 75, BUD 100, BUD 125, and BUD 100F) was measured for an average of 80-100 particles. A digital camera equipped with an optical microscope used to visualize the particles, and counted by advanced image analysis software. About 9-11 mg of microparticles (MPs) in 3 replicates were suspended and dissolved in 0.5 ml of acetonitrile by vortexing for 5 min. Then, 500 μl of the solution with 5-fold dilution were prepared and drug concentration in the replicates was measured using HPLC analysis (High Performance Liquid Chromatography) described below.

Figure 53:
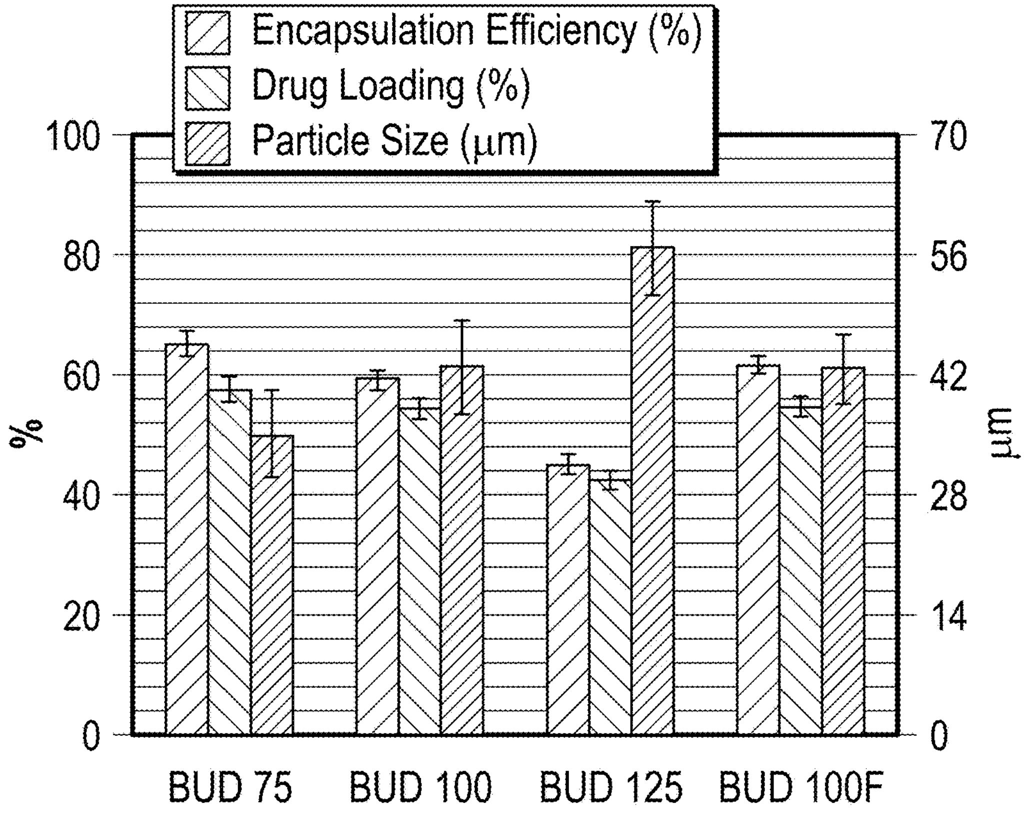
FIG. 53 illustrates drug loading and encapsulation efficacy parameters.

The obtained HPLC data were used to calculate drug loading and encapsulation efficacy parameters reported in FIG. 53, where Drug loading (%)=[mass of budesonide (mg) in MPs]/[mass of MPs (mg)]×100, and Encapsulation efficiency (%)=[mass of budesonide (mg) in MPs]/[theoretical mass of budesonide (mg) added initially]×100.

Budesonide kinetic release studies were analyzed using High-Performance Liquid Chromatography (HPLC). A 1260 Infinity II HPLC system equipped with a 1260 quaternary pump, 1260 Hip ALS autosampler, 1290 thermostat, 1260 TCC control module, and 1260 diode array detector. Data processing and analysis was performed using software. Budesonide chromatographic isocratic separation was carried out on an Agilent 4.6×150 mm Zorbax Eclipse XDB C-18 analytical column with 5 μm particles, maintained at 30° C. The optimized mobile phase consisted of 20 mM dipotassium phosphate buffer (pH 3.00 adjusted with phosphoric acid) and acetonitrile [30:70 (v/v)] at a flow rate of 1.00 mL/min over a 5 min run time. The injection volume was 5 μl and the selected ultraviolet (UV) detection wavelength was 244 nm at a bandwidth of 4.0, no reference wavelength, and an acquisition rate of 40 Hz.

Figure 54:
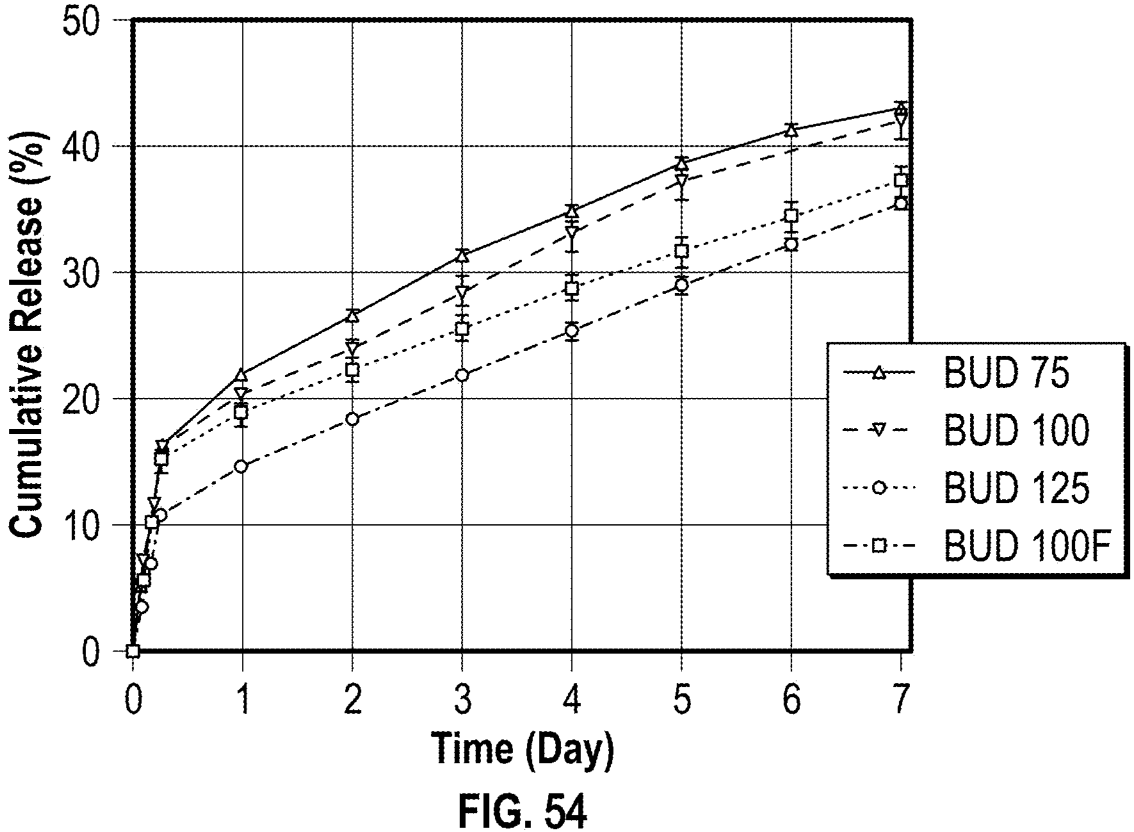
FIG. 54 illustrates a release profile of encapsulated budesonide.

Drug release occurs through polymeric membrane erosion, allowing the drug to diffuse out from the dialysis membrane. The in vitro release kinetics of budesonide from the PLGA particles in a biorelevant fluid, phosphate-buffered saline (PBS), were analyzed using High-Performance Liquid Chromatography. The in vitro release of budesonide from microparticles was performed using a horizontal shaker with 200 rpm speed at 37° C. Three to 5 milligrams of budesonide loaded microparticles were added to 1 ml phosphate buffered saline (PBS pH 7.4 (1×)) with 0.1% Tween 20. Experiments were performed at 37° and samples were taken at 2, 4, 6 h, and then daily up to 7 days of release. Buffer were refreshed at different time intervals and the drug content was analyzed using HPLC analysis of 500 μl of supernatant solution as described via High-Performance Liquid Chromatography analysis. Notably, the release profile of encapsulated budesonide demonstrated an initial burst release followed by linear drug release up to approximately 40% across all the formulations over 7 days of incubation in PBS at 37° C., as illustrated in FIG. 54.

Figure 55:
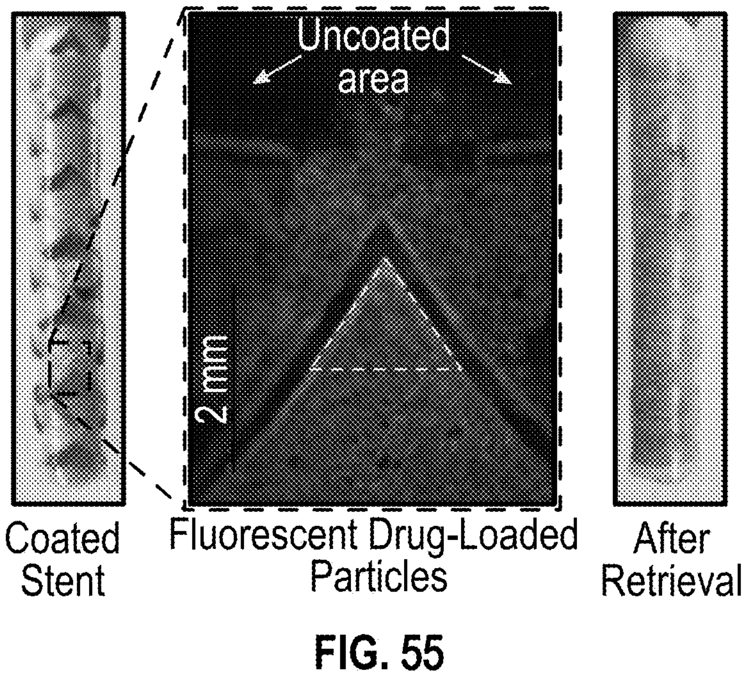
FIG. 55 illustrates images of coated kirigami-inspired stents and a magnified view of a needle surface/tip taken by a fluorescence microscope.

The needle surfaces/tips of kirigami stents were loaded by pipetting 20 μl of the BUD 100F particle solution two times per needle with a 5 h interval for drying at room temperature. FIG. 55 shows the coated kirigami stent and the magnified view of a needle surface/tip taken by a fluorescence microscope, showing consistent deposition of a uniform budesonide-PLGA microparticles layer onto the stent surface. Three esophageal kirigami stents with drug-loaded polymeric particles were delivered in vivo to the middle and distal esophagus of a large animal model (three Yorkshire pigs), and deposited drug particles via circumferential injections.

To evaluate the ability of kirigami stents, loaded with the budesonide-PLGA microparticles, to achieve long-term delivery, we administered them to a large animal model (three Yorkshire pigs). The details of delivery, deployment and removal of the stents were the same as fluorescent particle-loaded stents previously described. The three animals were euthanized at three different time points: 1 day, 3 days and 7 days after deployment/removal in compliance with the AVMA Guidelines on Euthanasia. Endoscopic evaluation of the esophagus over the course of the study was performed to further explore the esophagus and ensure the absence of any ulceration or injury. The esophagi of three pigs were harvested and 8 mm diameter biopsies were used to take biopsies at least seven needle penetration sites per retrieved esophagus. The penetration sites were recognized by using an IVIS Spectrum in vivo imaging system. Note that the drug-loaded particles (BUD 100F) were fluorescence-sensitive due to incorporation of Alexa Flour 647 C2 Maleimide. The biopsies were then frozen until extraction. Budesonide was extracted from esophageal tissue by placing each biopsy in 500 μl of 5% BSA in PBS and homogenizing two times by 6500 rpm for 30 seconds. A 100 μl fraction of the homogenate was collected. 50 μl of 5 μg/ml hydrocortisone in acetonitrile and 1 mL ethyl acetate was added for budesonide extraction. These samples were vortex and centrifuged for ten minutes at 13000 rpm. Following centrifugation, the supernatant was evaporated to dryness. Samples were reconstituted in 300 μl acetonitrile and 200 μl of the reconstitute were pipetted into a 96-well plate containing 200 μl of Nanopure water and used for ultraperformance liquid chromatography—tandem mass spectrometry (UPLC-MS/MS) analysis.

The esophagi was analyzed using ultraperformance liquid chromatography-tandem mass spectrometry (UPLC-MS/MS). The analysis was performed on a Waters ACQUITY UPLC-I-Class System aligned with a Waters Xevo-TQ-S mass spectrometer. Liquid chromatographic separation was performed on an ACQUITY UPLC Charged Surface Hybrid C18 (50 mm×2.1 mm, 1.7-μm particle size) column at 50° C. The mobile phase consisted of aqueous 0.1% formic acid and 10 mM ammonium formate solution (mobile phase A) and an acetonitrile: 10 mM ammonium formate and 0.1% formic acid solution [95:5 (v/v)] (mobile phase B). The mobile phase had a continuous flow rate of 0.6 ml/min using a time and solvent gradient composition. The initial composition (100% mobile phase A) was held for 1 min, after which the composition was changed linearly to 50% mobile phase A over the next 0.25 min. At 1.5 min, the composition was 20% mobile phase A, and at 2.5 min, the composition was 0% mobile phase A, which was held constant until 3 min. The composition returned to 100% mobile phase A at 3.25 min and was held at this composition until completion of the run, ending at 4 min, where it remained for column equilibration. The total run time was 4 min, and sample injection volume was 2.5 μl. The mass spectrometer was operated in the multiple reaction monitoring (MRM) mode. Sample introduction and ionization was by electrospray ionization (ESI) in the positive ionization mode. MassLynx 4.1 software was used for data acquisition and analysis. Stock solutions of budesonide and internal standard hydrocortisone were prepared in methanol at a concentration of 500 μg/ml. A twelve-point calibration curve was prepared in methanol ranging from 1 to 5000 ng/ml.

Figure 56:
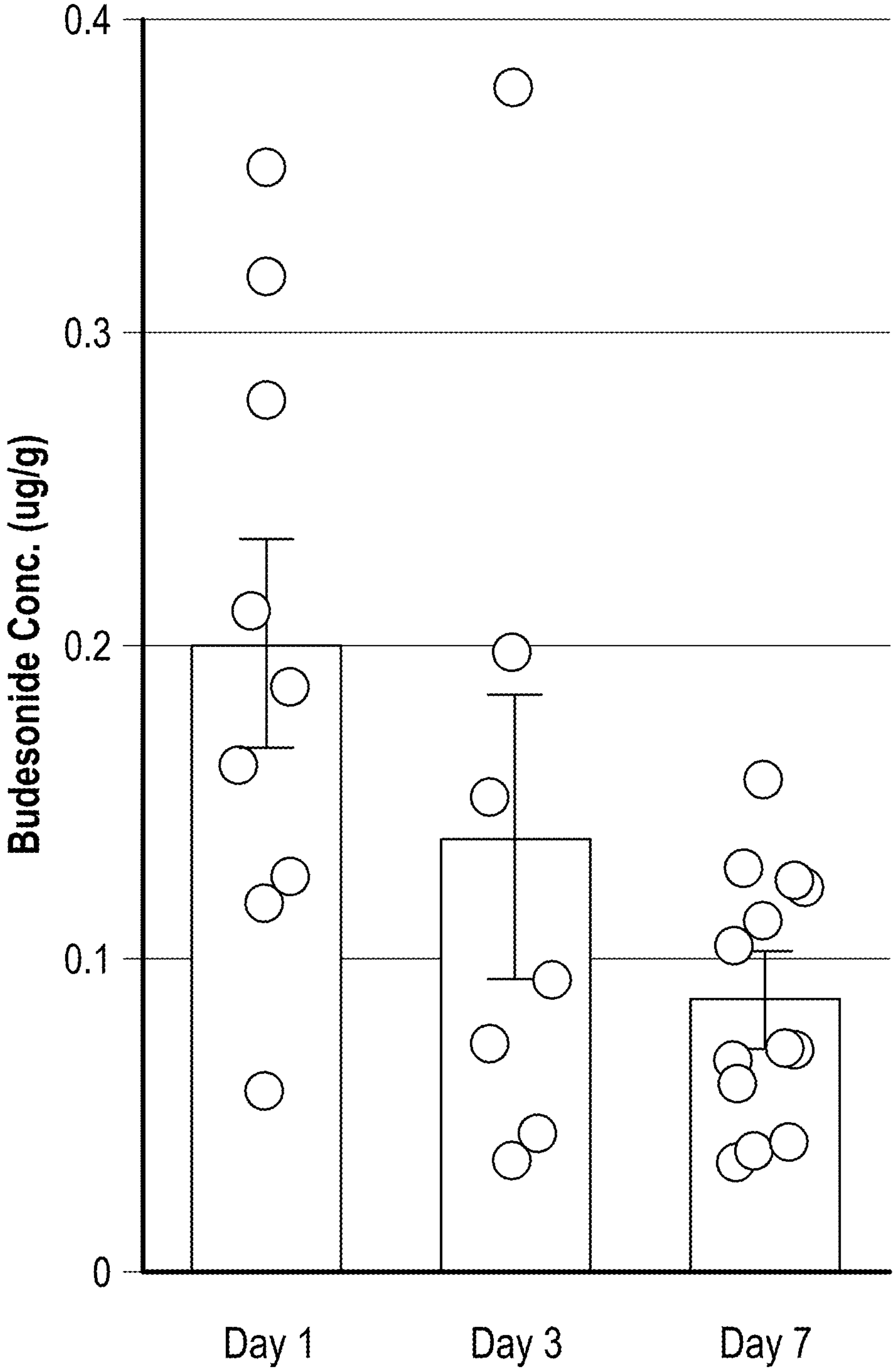
FIG. 56 illustrates a graph of concentrations of budesonide delivered using a kirigami-inspired stent.

The concentrations of budesonide delivered using the injectable stents are reported in FIG. 56. The data indicates that budesonide could be detected up to 0.09±0.02 μg/g per mass of tissue even after 7 days of the delivery, enabling sustained local delivery of budesonide and supporting the potential for this controlled drug releasing system to deliver drug agents to the tubular segments of GI tract.

Discussion.

In summary, given the importance of innovative device development, a class of drug releasing systems has been developed which are capable of multipoint injecting drug depots in the tubular mucosa of the GI tract such as the esophagus, enables sustained local drug delivery. Implementations of such a system were developed by: (i) design, FE modeling, and prototyping a kirigami-based stent platform and characterize the mechanics for robust deployment, multi-point injection, and safe removal in the tubular mucosa of the GI tract, and (ii) in vivo evaluation of the capacity to deposit drug-loaded polymeric particles for extended release using a large animal model. To develop the kirigami stent, first, buckling-induced kirigami surfaces were engineered to undergo a shape transformation from flat surfaces to 3D textured surfaces with popped-up needles. By turning kirigami surfaces to cylindrical kirigami skins, a systematic study was presented through combining FE simulations and experiments to investigate the effect of kirigami mesostructure (needle length and thickness) on the mechanical response of kirigami shells. Next, a fluid-powered elastomeric actuator was employed to generate linear output motion using a simple control input (i.e., pressurization of a working fluid) to trigger the kirigami shell for injection. By combining kirigami design principles and the pneumatic soft actuator a new way to deliver drug depots locally is provided and can be used to administer other APIs. Altogether, this design of injectable kirigami stent offers a unique mechanism with a range of advantages: (i) can be applied to various length-scales to be matched with the size of the target tubular compartments of the GI tract and airways; (ii) be able to rapidly deploy by more than 50% radial expansion and release therapeutics into submucosa through circumferential injections, and (iii) shape recovery to the original flat configuration by releasing the actuator pressure for safe removal.

Plasma surface treatment that activates the plastic kirigami surfaces and results in the creation of hydrophilic surfaces, and laser engraving the needle surfaces to increase surface area were used as two post-treatment techniques to improve adhesion bond between the coating layer (drug-particle solution) and kirigami stents needles that consequently enhance drug loading capacity. However, some drug particles may be lost by washing off the stent during delivery. Further studies on various polymeric or plastic surfaces to make the kirigami shell with enhanced drug loading capacity as well as polymeric sacrificial layers to protect the drug-coated particles, can be performed to further boost drug loading capacity and protected delivery without losing drug particles that finally leads to improved local drug delivery. Introducing a sheath will also protect the stent during delivery and eliminate the use of a separate introducer for facile delivery. Other designs including bi-material kirigami surfaces that includes plastic hinges to provide out of plane popping motion and insoluble drug-loaded needle tips for injection and deposit drug depots by dissolution into the mucosa could improve delivery performance, and reduce the risk of tissue inflammation, and safe removal. These technologies can be further improved through further in vivo testing of injectable kirigami stents with the aforementioned improved designs and evaluation sustained release within a target therapeutic range across different drugs depending on the target application sites. Another design of kirigami-based stents includes a design in which the kirigami spikes act as actuators to pop out and expose the attached small hypodermic needles for insertion. The hypodermic needles are connected via microchannels to the space inside the actuator as a drug reservoir to transfer liquid therapeutics.

While various spatial and directional terms, such as top, bottom, lower, mid, lateral, horizontal, vertical, front, and the like may be used to describe examples of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

Within this specification, embodiments have been described in a way which enables a clear and concise specification to be written, but it is intended and will be appreciated that embodiments may be variously combined or separated without parting from the invention. For example, it will be appreciated that all preferred features described herein are applicable to all aspects of the invention described herein.

Thus, while the invention has been described in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

Various features and advantages of the invention are set forth in the following claims.

What is claimed is:

1. A stent system for treating a submucosal tissue of a subject, the system comprising:

a tubular body extending along a central axis to form a lumen within the tubular body including two cutouts each coupled to a first end and a second end of the tubular body and configured as a first and second endcap of the tubular body, an actuator integrated within the lumen and configured to move the tubular body between a retracted position and an elongated position, wherein the tubular body encloses the actuator via the first and second endcaps; and a pattern of a plurality of cuts formed along the tubular body and extending through the tubular body to the lumen, wherein the pattern of the plurality of cuts deploy into a plurality of interconnected projections that are configured to extend radially away from the tubular body relative to the central axis to engage a submucosal tissue within the gastrointestinal tract or trachea of a subject when the tubular body is moved towards the elongated position.

2. The stent of claim 1, wherein when the tubular body is in the retracted position, the plurality of projections form a cylindrical outer surface of the tubular body.

3. The stent of claim 1, wherein the projections define a needle angle between about 1 degrees and about 90 degrees relative to the central axis when the projection is in a deployed position.

4. The stent of claim 1, wherein the projections are triangular-shaped, with a first edge and a second edge defining a cutting edge, and a base of the triangular-shaped projections defining an uncut portion of the tubular body.

5. The stent of claim 1, wherein the actuator is configured to elongate the tubular body to an elongated length that is between about 1% and about 100% greater than an initial length of the tubular body in the retracted position.

6. The stent of claim 1, wherein the actuator is a pneumatic actuator including an actuator body having an interior cavity and an inlet port, wherein the inlet port is configured to be in fluid communication with a pressurized fluid source to provide pressurized fluid to the interior cavity.

7. The stent of claim 6, wherein the pneumatic actuator comprises an elastomeric material.

8. The stent of claim 6, wherein the actuator body includes a fiber reinforcement extending along at least a portion of the length of the actuator body.

9. The stent of claim 8, wherein the fiber reinforcement includes strands of fibers arranged in a helical pattern.

10. A method of inserting a stent into a gastrointestinal tract or trachea a subject, the method comprising:

positioning a stent to a target tissue site within a gastrointestinal tract or trachea, the stent having a tubular body extending along a central axis to form a lumen within the tubular body including two cutouts each coupled to a first end and a second end of the tubular body and configured as a first and second endcap of the tubular body, pressurizing an actuator integrated within the lumen and to move the tubular body from a retracted position to an elongated position, wherein the tubular body encloses the actuator via the first and second endcaps, wherein a surface of the tubular body includes a pattern of a plurality of cuts configured to deploy into a plurality of interconnected projections as the tubular body is moved into the elongated position to engage the target tissue site of the subject.

11. The method of claim 10, wherein the projections are coated in a therapeutic agent such that the therapeutic agent is delivered to the subject when the projections engage the target tissue site.

12. The method of claim 11, wherein the stent is inserted in a first, insertion direction, and upon moving the tubular body into the elongated position, moving the stent in a second direction opposite the first direction to drive the projections into the target tissue site.

* * * * *